(12) United States Patent
Skolnik et al.

(10) Patent No.: US 9,457,016 B2
(45) Date of Patent: Oct. 4, 2016

(54) METHODS FOR TREATING POLYCYSTIC KIDNEY DISEASE

(71) Applicants: Edward Skolnik, New York, NY (US); Zhai Li, Rego Park, NY (US)

(72) Inventors: Edward Skolnik, New York, NY (US); Zhai Li, Rego Park, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/472,967

(22) Filed: Aug. 29, 2014

(65) Prior Publication Data
US 2015/0065486 A1    Mar. 5, 2015

Related U.S. Application Data

(60) Provisional application No. 61/871,621, filed on Aug. 29, 2013.

(51) Int. Cl.
| | | |
|---|---|---|
| A61K 31/433 | (2006.01) |
| A61K 31/501 | (2006.01) |
| C07D 285/135 | (2006.01) |
| A61P 31/12 | (2006.01) |
| A61K 45/06 | (2006.01) |
| A61K 31/198 | (2006.01) |
| A61K 31/4155 | (2006.01) |
| A61K 31/42 | (2006.01) |
| A61K 31/473 | (2006.01) |
| A61K 31/4738 | (2006.01) |
| A61K 31/55 | (2006.01) |
| A61K 9/00 | (2006.01) |
| A61K 47/06 | (2006.01) |
| A61K 9/06 | (2006.01) |
| A61K 9/08 | (2006.01) |
| A61K 9/20 | (2006.01) |
| A61K 9/48 | (2006.01) |

(52) U.S. Cl.
CPC .......... *A61K 31/433* (2013.01); *A61K 9/0014* (2013.01); *A61K 9/0019* (2013.01); *A61K 9/06* (2013.01); *A61K 9/08* (2013.01); *A61K 9/2063* (2013.01); *A61K 9/4866* (2013.01); *A61K 31/198* (2013.01); *A61K 31/4155* (2013.01); *A61K 31/42* (2013.01); *A61K 31/473* (2013.01); *A61K 31/4738* (2013.01); *A61K 31/55* (2013.01); *A61K 45/06* (2013.01); *A61K 47/06* (2013.01)

(58) Field of Classification Search
CPC .............. A61K 31/433; A61K 31/501; C07D 285/04; C07D 285/135
USPC .......... 514/363, 252.03, 252.05; 548/136, 139
See application file for complete search history.

(56) References Cited

U.S. PATENT DOCUMENTS

| | | |
|---|---|---|
| 6,451,828 B1 | 9/2002 | Newcomb et al. |
| 7,714,007 B2 | 5/2010 | Miller |
| 8,362,031 B2 | 1/2013 | Georg et al. |
| 8,604,016 B2 | 12/2013 | Li et al. |
| 2012/0220610 A1 | 8/2012 | Cerione et al. |
| 2012/0220619 A1 | 8/2012 | Farber et al. |
| 2013/0109643 A1 | 5/2013 | Riggins et al. |

FOREIGN PATENT DOCUMENTS

| | | |
|---|---|---|
| EP | 1185637 | 5/2000 |
| EP | 2550965 | 10/2008 |
| WO | 9811913 | 3/1998 |
| WO | 2012027537 | 3/2012 |
| WO | 2013078123 | 5/2013 |

OTHER PUBLICATIONS

Lukey et al. Future Med. Chem. 2013, 5 (14), 1685-1700.*
Wu et al., "Cardiac defects and renal failure in mice with targeted mutations in Pkd2", 2000, Nat. Genet. 24:75-78.
Guo et al., "A Cre recombinase transgene with mosaic, widespread tamoxifen-inducible action", Genesis, 2002, 32:8-18.
Ma et al., "Loss of cilia suppresses cyst growth in genetic models of autosomal dominant polycystic kidney disease", Nat Genet, 2013, 45:1004-1012.
Sweeney et al., "Src inhibition ameliorates polycystic kidney disease", J Am Soc Nephrol, 2008, 19:1331-1341.
Wilson et al., "Inhibition of HER-2(neu/ErbB2) restores normal function and structure to polycystic kidney disease (PKD) epithelia", Biochim Biophys Acta, 2006, 1762:647-655.
Yamaguchi et al., "Sorafenib inhibits cAMP-dependent ERK activation, cell proliferation, and in vitro cyst growth of human ADPKD cyst epithelial cells", Am J Physiol Renal Physiol, 2010, 299:F944-F951.
Qin et al., "c-Met and NF-κb-dependent overexpression of Wnt7a and -7b and Pax2 promotes cystogenesis in polycystic kidney disease", J Am Soc Nephrol, 2012, 23:1309-1318.
Torres et al. "Tolvaptan in patients with autosomal dominant polycystic kidney disease", The New England Journal of Medicine, 2012, 367:2407-2418.
Chapman, "Approaches to testing new treatments in autosomal dominant polycystic kidney disease: insights from the CRISP and HALT-PKD studies", Clinical Journal of the American Society of Nephrology, 2008, 3:1197-1204.
Shukla et al., "Design, synthesis, and pharmacological evaluation of bis-2-(5-phenylacetamido-1,2,4-thiadiazol-2-yl) ethyl sulfide (BPTES) analogs as glutaminase inhibitors", J Med Chem, 2012, 55:10551-10563.

(Continued)

*Primary Examiner* — Sreeni Padmanabhan
*Assistant Examiner* — Irina Neagu
(74) *Attorney, Agent, or Firm* — Klauber & Jackson LLC

(57) ABSTRACT

Methods for treating autosomal dominant polycystic kidney disease (ADPKD) are described herein. More particularly, methods described herein relate generally to administering glutaminase1 inhibitors to subjects afflicted with ADPKD. Accordingly, the use and application of compounds or agents that inhibit glutaminase1 for treating ADPKD or for use in a medicament for treating ADPKD are encompassed herein.

11 Claims, 15 Drawing Sheets

(56) References Cited

OTHER PUBLICATIONS

Wang et al., "Targeting mitochondrial glutaminase activity inhibits oncogenic transformation", Cancer Cell, 2010, 18: 207-219.
Katt et al, "Dibenzophenanthridines as inhibitors of glutaminase C and cancer cell proliferation", Mol Cancer Ther. 2012, 11:1269-1278.
Gross et al., "Antitumor activity of the glutaminase inhibitor CB-839 in triple-negative breast cancer", Mol Cancer Ther, 2014,13:890-901.
Thangavelu et al., "Structural basis for the allosteric inhibitory mechanism of human kidney-type glutaminase (KGA) and its regulation by Raf-Mek-Erk signaling in cancer cell metabolism", Proc Natl Acad Sci, 2012, 109:7705-7710.
Piontek et al., "A critical developmental switch defines the kinetics of kidney cyst formation after loss of Pkd1", Nat Med, 2007, 13:1490-1495.
Shibazaki et al., "Cyst formation and activation of the extracellular regulated kinase pathway after kidney specific inactivation of Pkd1", Hum Mol Genet, 2008, 17:1505-1516.
Patel et al., "Acute kidney injury and aberrant planar cell polarity induce cyst formation in mice lacking renal cilia", Hum Mol Genet, 2008, 17:1578-1590.
Shillingford et al., "The mTOR pathway is regulated by polycystin-1, and its inhibition reverses renal cystogenesis in polycystic kidney disease", 2006, Proc Natl Acad Sci, 103:5466-5471.
Karihaloo et al., "Macrophages promote cyst growth in polycystic kidney disease", J Am Soc Nephrol, 2011, 22:1809-1814.
Torres, "Treatment strategies and clinical trial design in ADPKD", Adv Chronic Kidney Dis, 2010, 17:190-204.
Yamaguchi et al., "Cyclic AMP activates B-Raf and ERK in cyst epithelial cells from autosomal-dominant polycystic kidneys", Kidney International, 2003, 63:1983-1994.
Duran et al., "Glutaminolysis Activates Rag-mTORC1 Signaling", Molec Cell, 2012, 47:349-358.
Gao et al., "c-Myc suppression of miR-23a/b enhances mitochondrial glutaminase expression and glutamine metabolism", Nature, 2009, 458:762-765.
Tao et al., "Rapamycin markedly slows disease progression in a rat model of polycystic kidney disease", J Am Soc Nephrol, 2005, 16:46-51.
Gattone et al., "Late progression of renal pathology and cyst enlargement is reduced by rapamycin in a mouse model of nephronophthisis", Kidney Int, 2009, 76:178-182.
Seltzer et al., "Inhibition of glutaminase preferentially slows growth of glioma cells with mutant IDH1", Cancer Research, 2010, 70:8981-8987.
Cao et al., "Chemical modifier screen identifies HDAC inhibitors as suppressors of PKD models", Proc Natl Acad Sci, 2009, 106:21819-21824.
Zhou et al., "Sirtuin 1 inhibition delays cyst formation in autosomal-dominant polycystic kidney disease", J Clin Invest, 2013, 123:3084-3098.
Li et al., "A tumor necrosis factor-alpha-mediated pathway promoting autosomal dominant polycystic kidney disease", Nat Med, 2008, 14:863-868.
Lu et al., "Cancer metabolism: Is glutamine sweeter than glucose?", Cancer Cell, 2010, 18:199-200.
Sweeney et al., "Treatment of polycystic kidney disease with a novel tyrosine kinase inhibitor", Kidney Int, 2000, 57:33-40.

\* cited by examiner

Figure 6
A
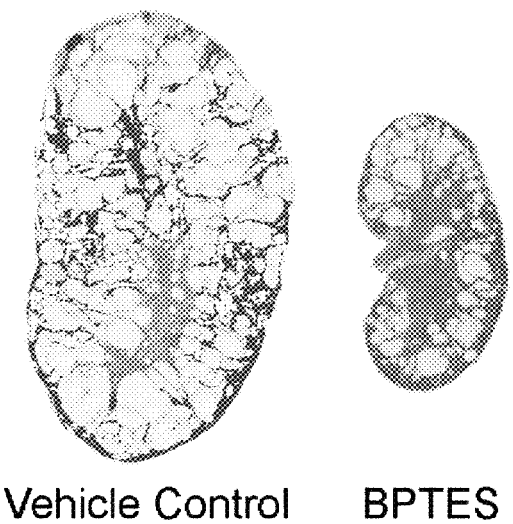
Vehicle Control    BPTES
B
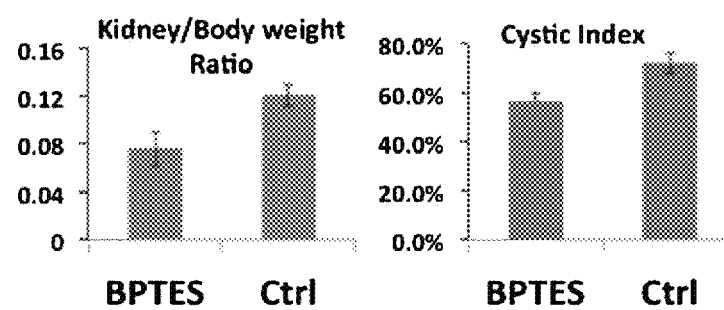

Figure 12
A
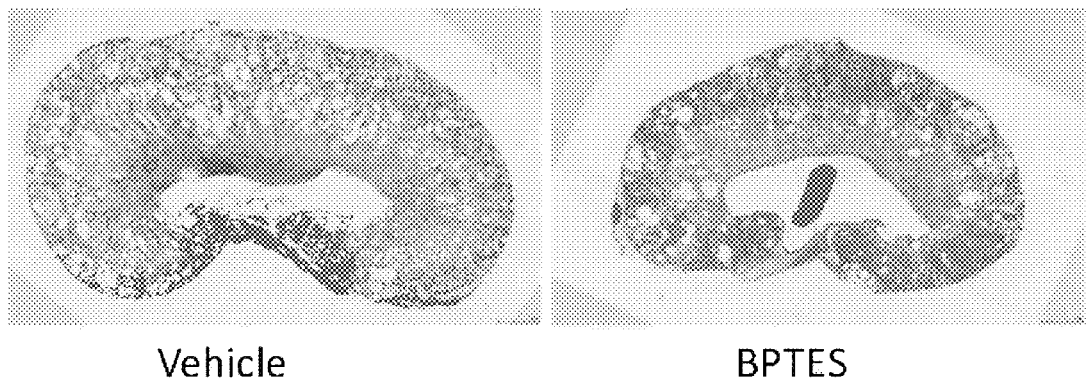
Vehicle　　　　　　　BPTES
B
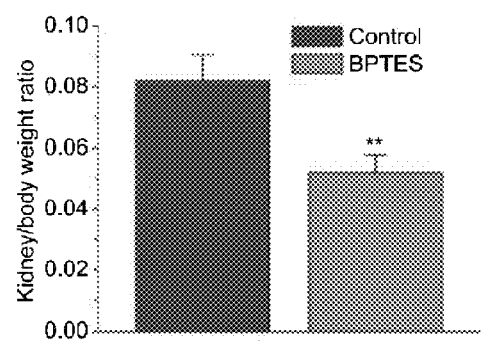
C
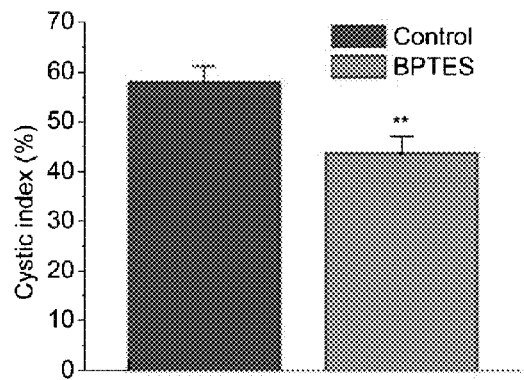

Figure 13
A
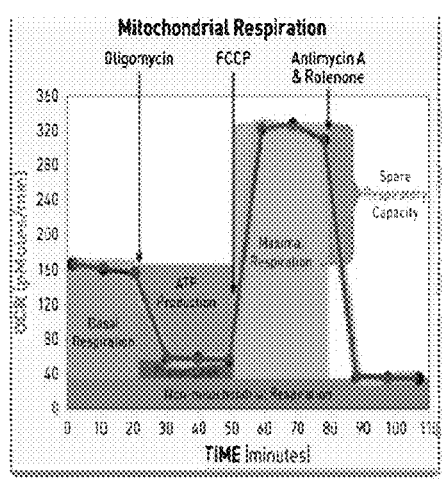
B
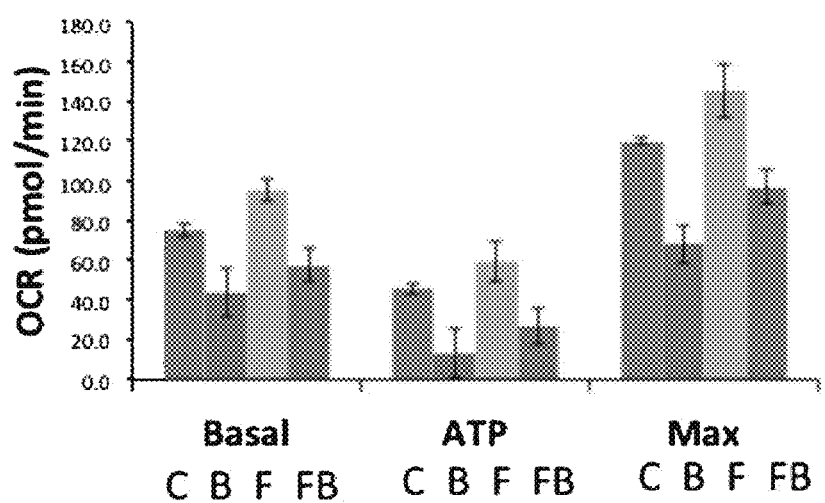

Figure 15
A
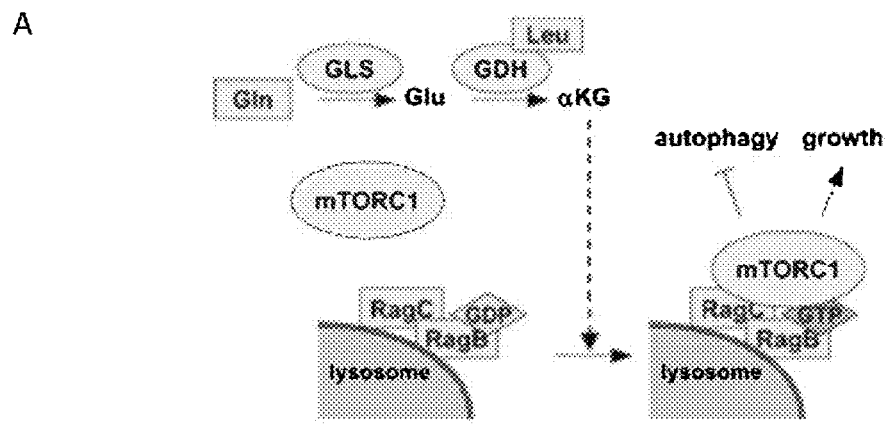
B
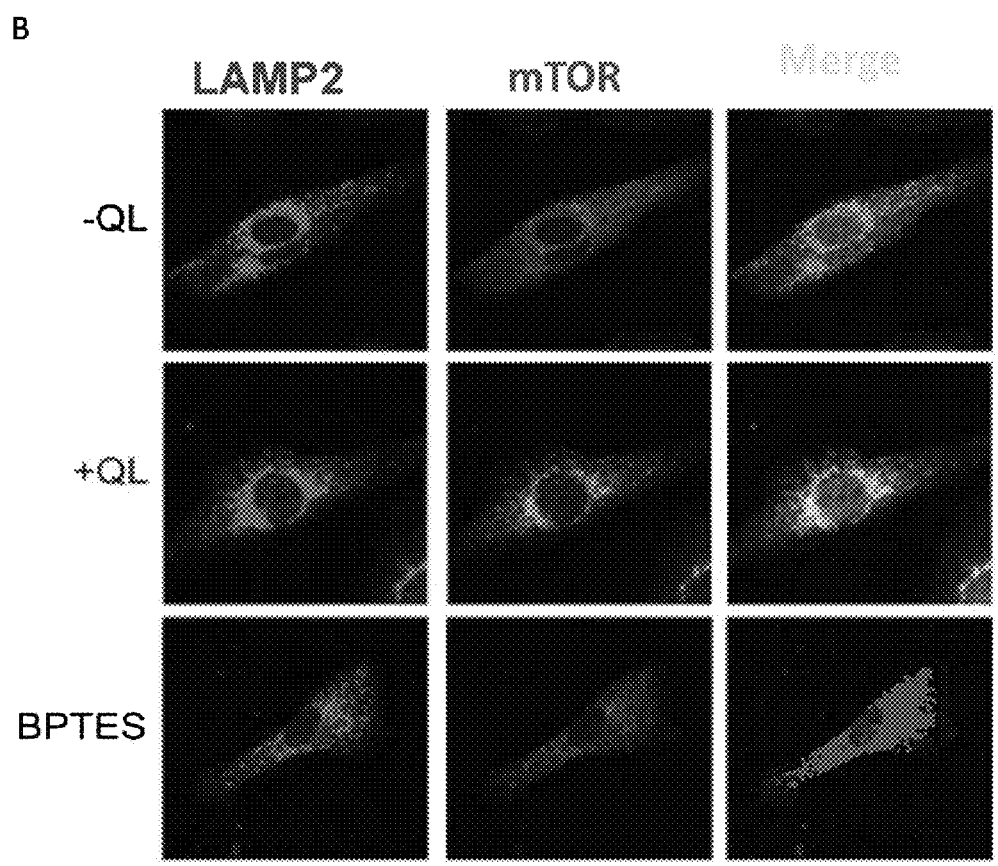

```
SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Synthetic siRNA

<400> SEQUENCE: 1
atggtggttt ctgcccaatt a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic combined DNA/RNA hybrid siRNA

<400> SEQUENCE: 2
gauggauugu uguaauggut t                                              21

<210> SEQ ID NO 3
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 3
accauuacaa caauccauc                                                 19

<210> SEQ ID NO 4
<211> LENGTH: 21
<212> TYPE: DNA
<213> ORGANISM: Artificial Sequence
<220> FEATURE:
<223> OTHER INFORMATION: Synthetic combined DNA/RNA hybrid siRNA

<400> SEQUENCE: 4
cauucuacug gagauaccat t                                              21

<210> SEQ ID NO 5
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 5
ugguaucucc aguagaaug                                                 19
```

US 9,457,016 B2

METHODS FOR TREATING POLYCYSTIC KIDNEY DISEASE

CROSS REFERENCE TO RELATED APPLICATIONS

This application claims priority under 35 USC §119(e) from U.S. Provisional Application Ser. No. 61/871,621, filed Aug. 29, 2013, which application is herein specifically incorporated by reference in its entirety.

FIELD OF THE INVENTION

Methods presented herein relate to agents for treating polycystic kidney disease (PKD), and more specifically to the novel use of inhibitors of glutaminase 1 activity for treating PKD and in the preparation of medicaments for use in the treatment of PKD. Methods presented herein relate generally to the treatment of PKD. In a particular embodiment the methods, agents, and medicaments are directed to treating autosomal-dominant polycystic kidney disease (ADPKD).

BACKGROUND OF THE INVENTION

ADPKD affects more than 12 million people worldwide and is a common cause of end stage kidney disease. In the majority of cases, ADPKD is caused by mutations in one of two genes, PKD1 or PKD2, which are encoded by polycystin 1 (PC1) and PC2, respectively. Loss of both copies of PC1 or PC2 is associated with cyst formation and cyst enlargement by stimulating the enhanced growth of renal epithelia as well as the stimulation of apical chloride secretion via the cystic fibrosis transmembrane conductance regulator (CFTR). Over time, cysts become more numerous and larger in size and replace normal kidney tissue leading to loss of renal function.

The citation of references herein shall not be construed as an admission that such is prior art to the present invention.

SUMMARY OF THE INVENTION

The present inventors have made the surprising discovery that inhibiting glutaminase 1 either pharmacologically or via siRNA blocks cyst formation and proliferation of primary cells isolated from patients with ADPKD. Based on these results, the present inventors propose that inhibiting glutaminase 1 provides a novel therapy to slow growth of cysts in vivo and thereby slow progression of kidney disease in patients with ADPKD.

In accordance with these findings, a method for treating autosomal dominant polycystic kidney disease is described herein, the method comprising administering to a subject in need thereof a therapeutically effective amount of an inhibitor of glutaminase 1 activity or a composition thereof.

Also encompassed herein is a method for inhibiting growth of kidney cysts in a subject afflicted with autosomal dominant polycystic kidney disease, the method comprising administering to a subject in need thereof a therapeutically effective amount of an inhibitor of glutaminase 1 activity or a composition thereof.

In a further aspect, a method for slowing progression of kidney disease in a subject afflicted with autosomal dominant polycystic kidney disease is presented, the method comprising administering to a subject in need thereof a therapeutically effective amount of an inhibitor of glutaminase 1 activity or a composition thereof.

In a particular embodiment, the inhibitor of glutaminase 1 activity acts directly on glutaminase 1 protein. Such inhibitors act directly on glutaminase 1 protein by reducing activity of the protein. In certain circumstances, an inhibitor of glutaminase 1 activity may bind to glutaminase 1.

In a particular embodiment, the inhibitor of glutaminase 1 activity administered acts directly on glutaminase 1. Exemplary glutaminase 1 inhibitors comprise bis-2-(5-phenylacetamido-1,2,4-thiadiazol-2-yl)ethyl sulfide (BPTES) and analogs thereof; N-(5-{2-[2-(5-amino-[1,2,4]thiadiazol-2-yl)-ethylsulfanyl]-ethyl}-[1,3,4]thiadiazol-2-yl)-2-phenyl-acetamide; small molecule 968 and derivatives thereof 6-diazo-5-oxo-L-norleucine (DON); N-ethylmaleimide (NEM); p-chloromercuriphenylsulfonate (pCMPS); L-2-amino-4-oxo-5-chloropentoic acid; DON plus o-carbamoyl-L-serine; acivicin [(alphaS,5S)-alpha-amino-3-chloro-4,5-dihydro-5-isoxazoleacetic acid]; azaserine; and 5-(3-bromo-4-(dimethylamino)phenyl)-2,2-dimethyl-2,3,5,6-tetrahydrobenzo[-a]phenanthridin-4(1H)-one.

In a more particular embodiment, the inhibitor of glutaminase 1 activity is BPTES or an analog thereof.

In a particular embodiment of the method, the subject afflicted with autosomal dominant polycystic kidney disease is a mammal. In a more particular embodiment, the mammal is a human.

In a more particular embodiment, the method further comprises administering a therapeutically effective amount of at least one therapeutic agent selected from the group consisting of a vasopressin receptor antagonist, an HDAC inhibitor, a Src inhibitor, a Sirtuin 1 inhibitor, a tumor necrosis factor inhibitor, an epidermal growth factor inhibitor, an epidermal growth factor receptor inhibitor, a HER2 inhibitor, a Braf inhibitor, an inhibitor of hepatocyte growth factor, and an inhibitor of hepatocyte growth factor receptor cMET. In a more particular embodiment, the vasopressin receptor antagonist is tolvaptan or a mTor inhibitor.

In a particular embodiment, the inhibitor of glutaminase 1 activity or the composition thereof is administered orally or intraperitoneally.

In another particular embodiment, the subject is evaluated to determine if glutaminase 1 activity is elevated in the kidneys of the subject. Such a determination may be made before, during, or after initiation of a therapeutic regimen as described herein. In advance of treatment, such an evaluation may be used to predict efficacy of the therapeutic regimen. Under such a circumstance, a subject having elevated kidney glutaminase 1 activity is predicted to respond favorably to the present therapeutic regimens. When performed during the course of a therapeutic regimen described herein, such an evaluation may be used to determine efficacy of the therapeutic regimen on an ongoing basis and may, moreover, provide guidance as to whether adjustments in the dosing of therapeutic agents is advisable. When performed after a therapeutic regimen described herein, such an evaluation may be used to monitor the patient to ensure that normal kidney function is maintained or additional therapeutic measures are merited.

Other objects and advantages will become apparent to those skilled in the art from a review of the following description which proceeds with reference to the following illustrative drawings.

BRIEF DESCRIPTION OF THE DRAWINGS

FIG. 6A-B. Inhibition of Gls1 with BPTES significantly decreases kidney size and cyst volume in an animal model of ADPKD. Pkd1$^{fl/fl}$; Pkhd1-Cre mice were treated by intraperitoneal injection every other day (QOD) with 200 µl BPTES (12.5 mg/kg body weight) or vehicle control starting postnatal day 10 until postnatal day 24 when mice were sacrificed. (A) Shown is a representative example of a scan of a sagittal section of kidneys from 4 control and 4 BPTES treated mice. (B) Kidney size and cyst volume were significantly decreased in BPTES treated mice relative to control treated mice.

FIG. 12A-C. Treatment of Tamoxifen-Cre; PKD1$^{fl/fl}$ mice with BPTES slows cyst growth in vivo. Cre was induced at postnatal day 10 with tamoxifen 10 mg/40 mg IP×2 and mice were then treated with BPTES (12.5 mg/kg IP BID) or vehicle control between postnatal day 15-32 (n=4). Mice were sacrificed on day 32 and analyzed. (A) Scan of sagittal section of littermates treated with BPTES or vehicle control; (B) Kidney wt/body wt; (C) cystic index.

FIG. 13A-B. Seahorse analysis of ADPKD cells. ADPKD cells that were unstimulated or stimulated with forskolin in the presence or absence of BPTES and mitochondrial oxygen consumption was determined by seahorse analysis. (A) Schematic of the method and analysis. Oligomycin inhibits ATP synthase. FCCP is a mitochondrial uncoupler and leads to maximal OCR and rotenone interferes with electron transport. (B) Inhibition of ATP generation was also found by Seahorse analysis. ADPKD cells were unstimulated in the absence (C) or presence of BAPTES (B) or stimulated with forskolin in the absence (F) or presence of BPTES (FB).

FIG. 15A-B. BPTES prevents recruitment of mTor to lysosomal compartment. (A) Schematic depicting mTor activation, which is mediated by the recruitment of mTor to the lysosome. (B) ADPKD cells were stimulated as in FIG. 14 and then subjected to immunofluorescence analysis with antibodies to LAMP (lysosomal associated membrane protein) which stains lysosomes and mTor. Co-localization is shown by a yellow signal following the merging of the green mTor signal and the red LAMP signal. Refeeding with amino acids (QL) led to colocalization or recruitment of mTor to the lysosome as manifested by yellow staining in the merged image (compare –QL with +QL), which was abolished by treatment with BPTES.

DETAILED DESCRIPTION

Figure 1:
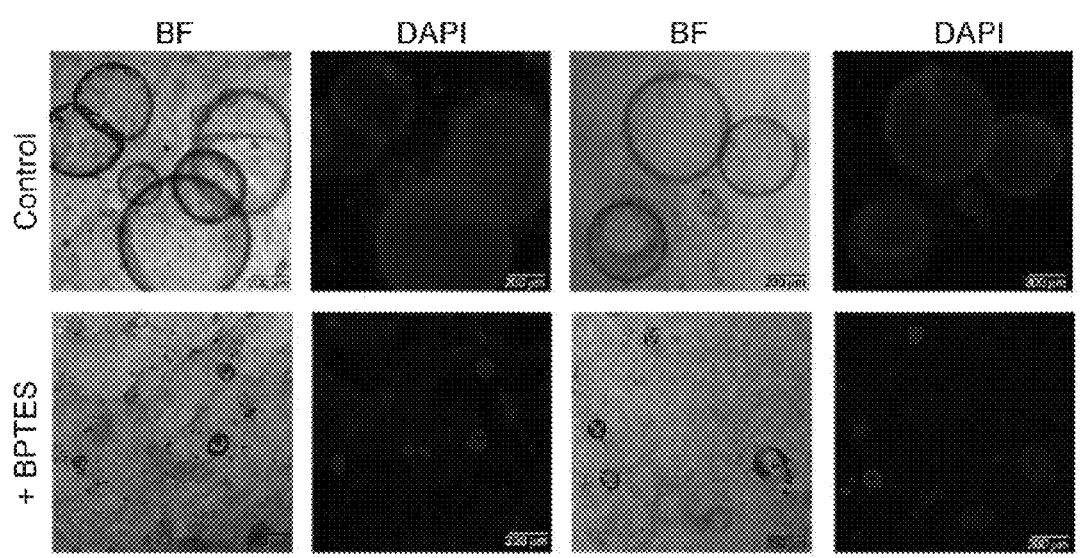
FIG. 1. Glutaminase 1 inhibitor (BPTES) blocks cyst formation of ADPDK cells. ADPKD cells were plated in collagen and stimulated with forskolin in the presence (BPTES) or absence (Control) of the gls1 inhibitor BPTES. Images are at 10×. BF=bright field.

The kidneys perform a variety of essential functions, including filtration of wastes from the blood and concentration of such wastes in urine for subsequent elimination from the body. Their role in maintaining osmotic balance is, moreover, underscored by their ability to remove excess water from the bloodstream, which is also eliminated via urine excretion. The kidneys also regulate retention of physiological levels of sodium, potassium, and phosphorus in the body. Preserving kidney function is, therefore, critical for maintaining normal physiology.

PKD is a genetic disorder characterized by the growth of numerous fluid-filled cysts in the kidneys. During the course of disease progression, PKD cysts grow and supplant normal kidney tissue, leading to reduced kidney function and ultimately, kidney failure. The cysts are, moreover, numerous and fluid-filled, which causes massive enlargement of the kidneys. PKD can also lead to the formation of hepatic cysts, pancreatic cysts, splenic cysts, ovarian cysts, and/or prostatic cysts and, in rare cases, to problems in other organs, such as the heart and blood vessels of the brain.

The terms end-stage kidney disease or end-stage renal disease (ESRD) are used to refer to the complete or almost complete failure of kidney function. When PKD leads to ESRD in a patient, the patient will have to undergo regular dialysis or receive a kidney transplant in order to survive.

There are two types of heritable PKD: ADPKD and the less common autosomal recessive polycystic kidney disease (ARPKD). ADPKD is one of the most common monogenic hereditary diseases. It affects 1 to 2:1,000 live births (Bisceglia et al. 2006, Adv Anatomic Pathol 13:26-56; Simons et al. 2006 Kidney International 70:854-864; Yersin et al. 1997 Nephrol Dial Transplant 12:2069-2074). The most prevalent and obvious symptom of ADPKD is the formation of kidney cysts, which result in grossly enlarged kidneys and impaired kidney function that impacts the ability of the kidneys to filter and concentrate bodily fluids. ADPKD-associated renal cysts may comprise several liters of fluid, which in turn causes engorgement of the kidneys and pain. Initial simian and human symptoms of ADPKD include hypertension, fatigue, and mild to severe back or flank pain and urinary tract infections. The disease is also characterized by epithelial cell proliferation.

Autosomal recessive polycystic kidney disease (ARPKD) is much rarer than ADPKD and is often fatal in utero or during the first month of life. The signs and symptoms of the condition are usually apparent at birth or in early infancy.

In light of the high frequency of PKD, especially with respect to ADPKD, and the absence of an effective therapeutic regimen to impair or reverse disease progression, there is an imperative to identify agents that can be used to treat patients afflicted with PKD. The need for a therapeutic regimen for ADPKD is underscored by the fact that there is no approved treatment for ADPKD that slows the growth of renal cysts and delays the time to end-stage kidney disease.

Great strides have been made in the past 10-20 years to identify alterations in signaling pathways that contribute to growth of PKD cells and cysts in vivo. Recent evidence has indicated that cells undergoing increased growth and division exhibit marked changes in cellular metabolism. Importantly, changes in metabolism that are necessary for increased cell growth, intersect with known signaling pathways and transcription factors that have been implicated in cell proliferation. In this regard, glucose and glutamine are two major substrates for proliferating cells that provide ATP, carbon skeletons, and nitrogen required for macromolecular synthesis and cell growth. The present inventors hypothesized that glutamine metabolism may play a critical role in proliferation of ADPKD cells, but not normal human kidney cells, and that drugs that interfere with glutamine metabolism will slow cyst growth and loss of renal function in patients with ADPKD. Results presented herein support this prediction.

Glutaminase1 is one of the key enzymes required for glutamine metabolism. Glutaminase1 (gls1) converts glutamine to glutamate, which is subsequently converted to α-ketoglutarate, a key intermediate leading to ATP generation as well as the carbon backbone for cellular anabolic processes. Results presented herein demonstrate that inhibiting glutaminase 1 slows cyst growth and proliferation of ADPKD cells indicating that pharmacologically inhibiting glutaminase 1 is a novel treatment to slow cyst growth and progression to end stage kidney disease in patients with ADPKD.

Figure 2:
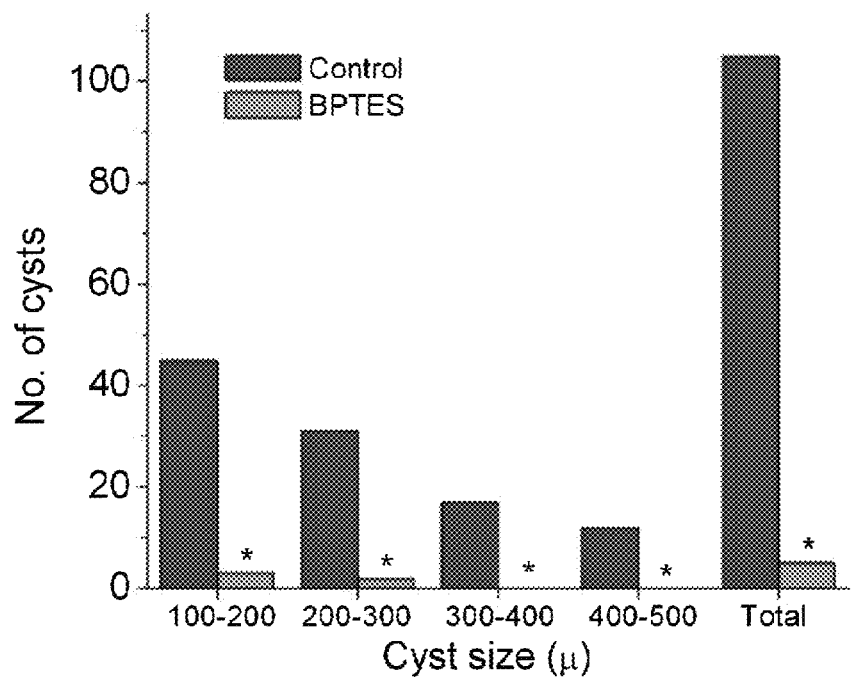
FIG. 2. Quantification of cyst size and cyst number in ADPKD cells incubated with or without BPTES. Total number of cysts in FIG. 1 was counted and stratified by cyst size. Asterisks indicate statistically significant findings.

More particularly, results depicted in FIGS. 1 and 2 show that inhibition of gls1 blocks cyst formation in vitro in ADPKD cells. As described herein, an exemplary gls1 inhibitor BPTES bis-2-(5-phenylacetamido-1,2,4-thiadiazol-2-yl)ethyl sulfide inhibited cyst formation in ADPKD cells. FIG. 1 presents photomicrographs that illustrate the dramatic reduction in both the number and size of cysts observed in cultures treated with BPTES. FIG. 2 presents the results of these experiments graphically, which presentation underscores that the decrease in the number of observable cysts and the size of detected cysts is statistically significant.

Figure 3:
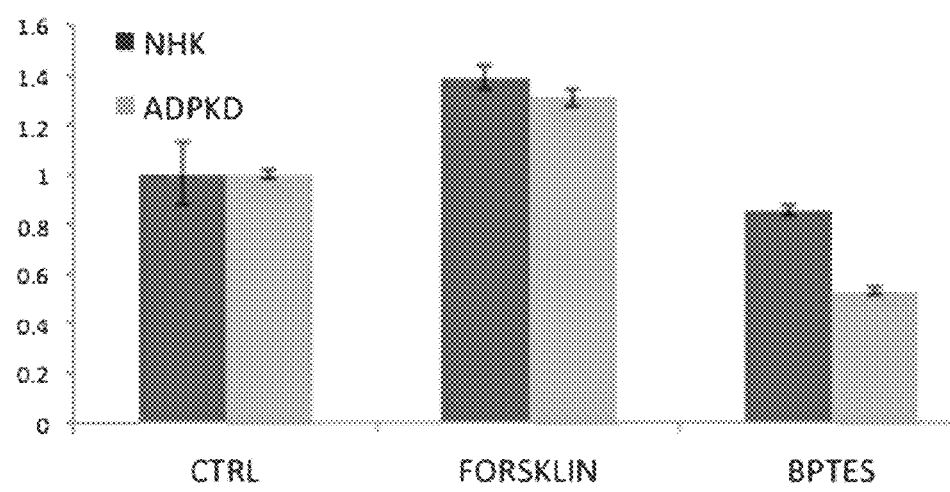
FIG. 3. Inhibition of Gls1 with BPTES inhibits proliferation of ADPKD cells. ADPKD or NHK cells were serum starved for 24 hours and then either untreated or treated with forskolin in the presence of absence of BPTES. Proliferation was then quantitated 24 hours later using the MTT assay kit (Promega).

Results depicted in FIG. 3 demonstrate that inhibition of gls1 with BPTES markedly decreases forskolin-induced proliferation of ADPKD cells. Evidence presented herein, furthermore, suggests that the decrease in proliferation of ADPKD cells by BPTES is due to direct effects on gls1 inhibition, rather than due to the nonspecific inhibition of another signaling pathway.

Figure 4:
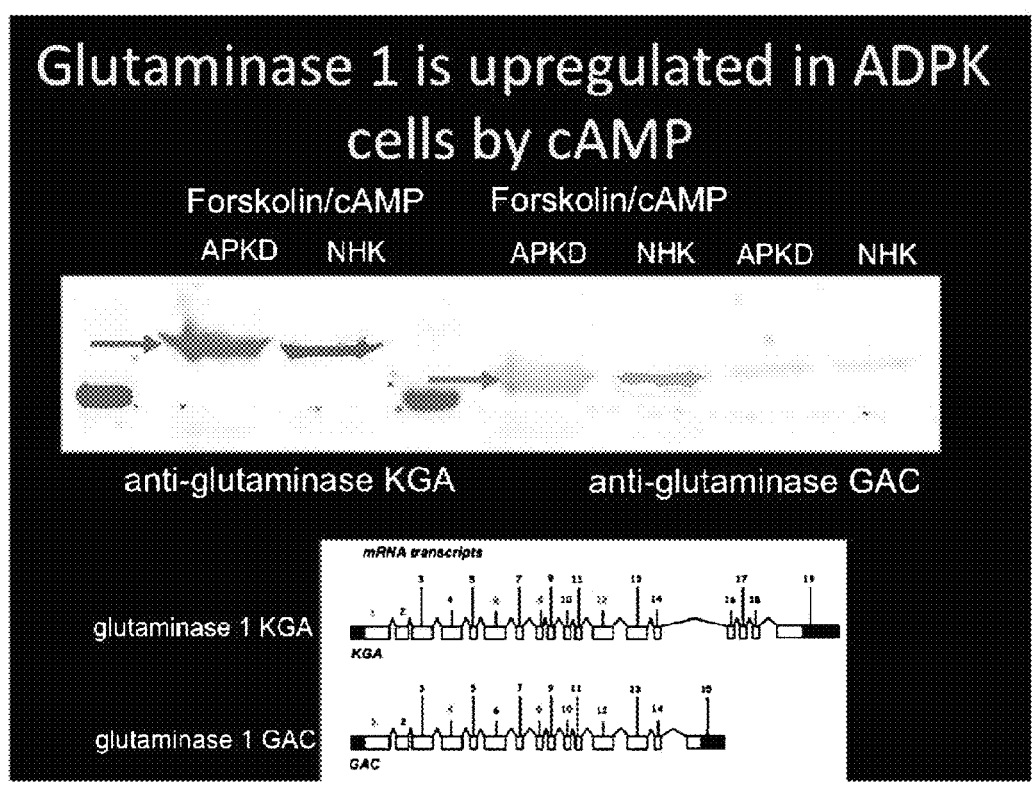
FIG. 4. Increased protein expression of Glutaminase following treatment with the cAMP activator forskolin. ADPKD or NHK cells were either unstimulated or stimulated with forskolin to increase cAMP. 24 hours later, cells were lysed and immunoblotted with anti-glutaminase 1 antibodies that recognized either the KGA or GAC g1 isoform.

Results depicted in FIG. 4 also show that gls1 is important for ADPKD cell proliferation. Indeed, the percent increase in gls1 isoforms following forskolin stimulation is markedly higher than that observed in normal human kidney (NHK) cells.

Figure 5:
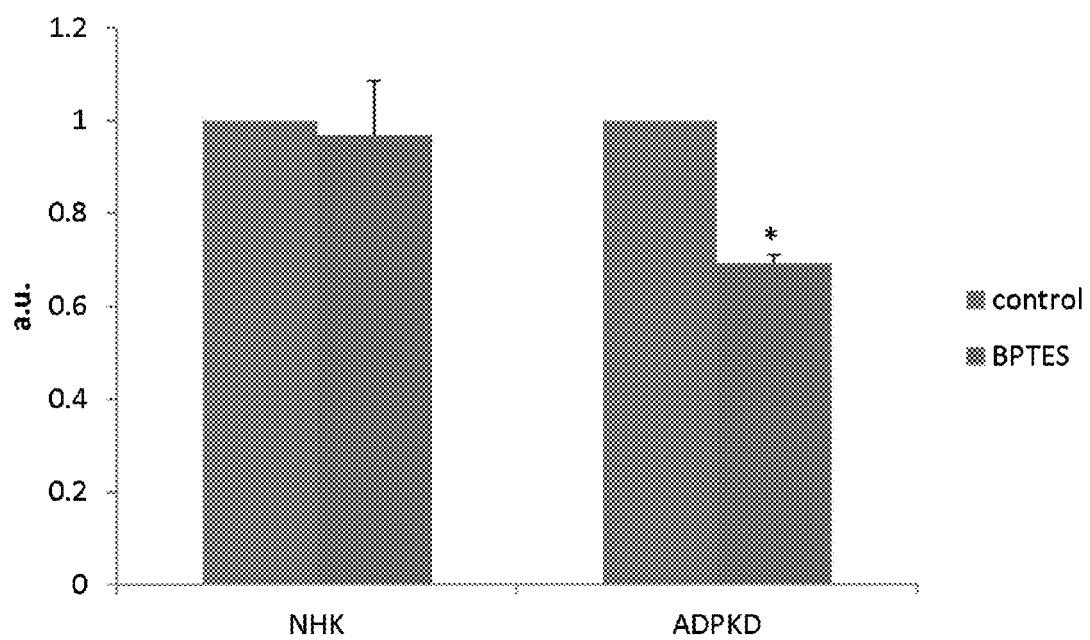
FIG. 5. Inhibition of Gls1 with BPTES inhibits ATP generation in ADPKD cells. ADPKD or NHK cells were untreated or treated with BPTES and intracellular ATP levels were determined 24 hours later.

Results depicted in FIG. 5 reveal that treatment of ADPKD cells with BPTES results in a statistically significant decrease in intracellular ATP levels in ADPKD cells. These findings support the contention that glutamine is an important source for ATP, particularly in ADPKD cells.

Results depicted in FIG. 6 demonstrate that inhibition of Gls1 following administration of BPTES significantly decreases kidney size and cyst volume in $Pkd1^{fl/fl}$; Pkhd1-Cre mice, an animal model of ADPKD. As shown therein, kidney size and cyst volume were significantly decreased in BPTES treated mice relative to control treated mice. It is also noteworthy that some preservation/restoration of kidney function was observed following BPTES administration. BPTES is, moreover, known to inhibit both isoforms of Gls1. These results underscore the potential for efficacious use of Gls1 inhibitors for treating ADPKD in humans. These findings apply to Gls1 inhibitors in general, particularly those that comprise the BPTES backbone chemical structure, as well as BPTES.

Figure 7:
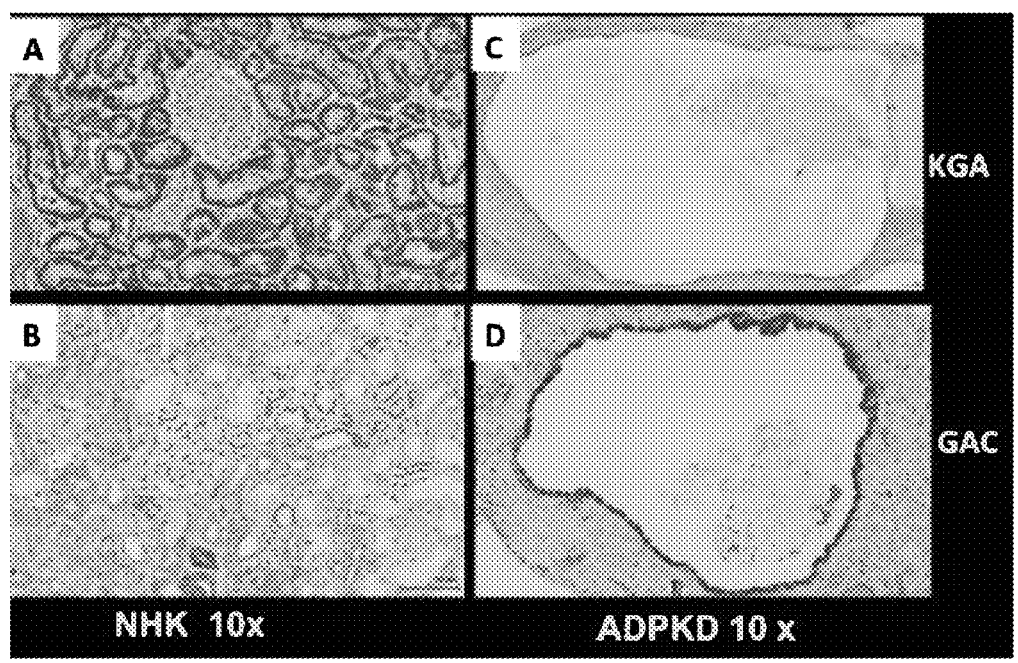
FIG. 7A-D. Expression of Gls1 KGA and CAG isoforms in normal human (NHK) and ADPKD kidneys. NHK (A,B) and ADPKD (C,D) kidneys were probed with anti-Gls1 KGA (A,C) or anti-Gls1 GAC (B,C). KGA, which is important for acid secretion and generation of NH4$^+$ by the proximal tubule, is expressed at high levels in normal kidney (A). Very little of the CAG isoform is expressed in NHK (B). Importantly, GAC is markedly upregulated in cyst lining epithelia in ADPKD kidneys (D) compared to KGA (C). Shown is a representative example of >70% of cyst lining epithelia.

FIG. 7 presents the results of immunohistochemistry experiments, which reveal the expression pattern of Gls1 KGA and CAG isoforms in normal human (NHK) and ADPKD kidneys. Gls1 exists in 2 isoforms depending on whether exon 14 is spliced to exon 15 (GAC isoform) or whether exon 14 is spliced directly to exon 16 (KGA isoform) (see FIG. 4, bottom). The KGA isoform is widely expressed and is the major form expressed in the kidney, wherein it is responsible for generating $NH4^+$ for acid secretion. In contrast, expression of the GAC isoform is much more limited and GAC is often upregulated in cancer cells where it is the predominate isoform that regulates glutaminolysis. In agreement with the literature, the present inventors found that KGA is the predominant isoform expressed in tubule cells of normal human kidney (NHK), while GAC expression was much more limited (FIG. 7, A,B). In contrast, the present inventors found marked upregulation of GAC in >70% of cyst lining epithelia in ADPKD kidneys (FIG. 7, C,D).

Figure 8:
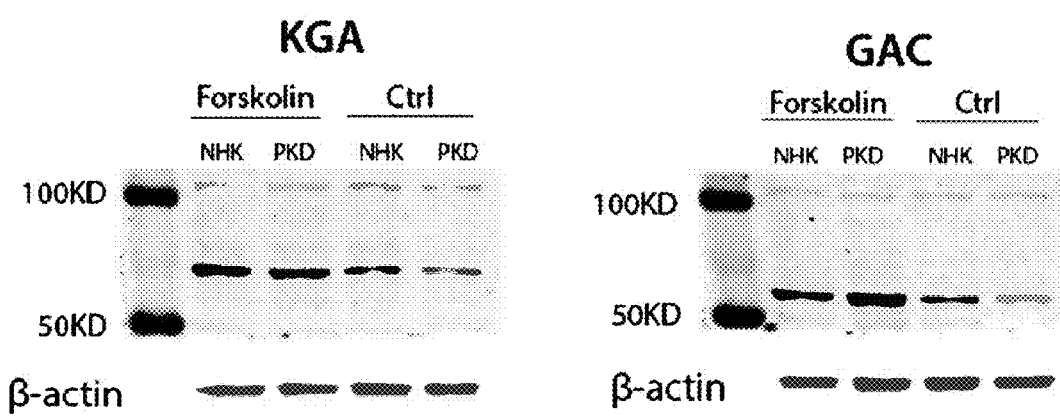
FIG. 8. ADPKD and NHK cells express both the GAC and KAG isoforms of Gls1. NHK or ADPK cells were cultured for 24 hours in the presence or absence of forskolin and then immunoblotted with antibodies that specifically recognize the GAC or KAG isoforms of Gls1. Lysates were probed with β-actin to verify similar loading between lanes.

FIG. 8 depicts a Western blot showing that ADPKD and NHK cells express both the GAC and KAG isoforms of Gls1. In order to study Gls1 and the role of glutaminolysis in vitro, the present inventors obtained primary human ADPKD and NHK (normal human kidney) cells from Darren Wallace (Univ. of Kansas). As shown in FIG. 8, both KGA and GAC isoforms of Gls1 are expressed in NHK and ADPKD cells. Protein expression of the GAC isoform and to a lesser extent the KGA isoform were increased in several ADPKD cell lines (4/6) following forskolin stimulation, which is a potent cAMP agonist (FIG. 8). While both Gls1 isoforms were also increased in NHK cells, the relative increase was generally less for GAC when compared with that observed in ADPKD cells (FIG. 8). These findings are intriguing in light of previous findings that elevated levels of cyclic 3'-5'-adenosine monophosphate (cAMP) are found in $PKD^{-/-}$ cells and contribute to cyst growth by stimulating cell proliferation via activation of Src and B-Raf signaling pathways and via Cl⁻ secretion via the CFTR (Chapman et al. 2008, Clin J Amer Soc Nephrol 3:1197-1204; Torres et al. 2010, Adv Chronic Kidney Dis 17:190-204).

Figure 9:
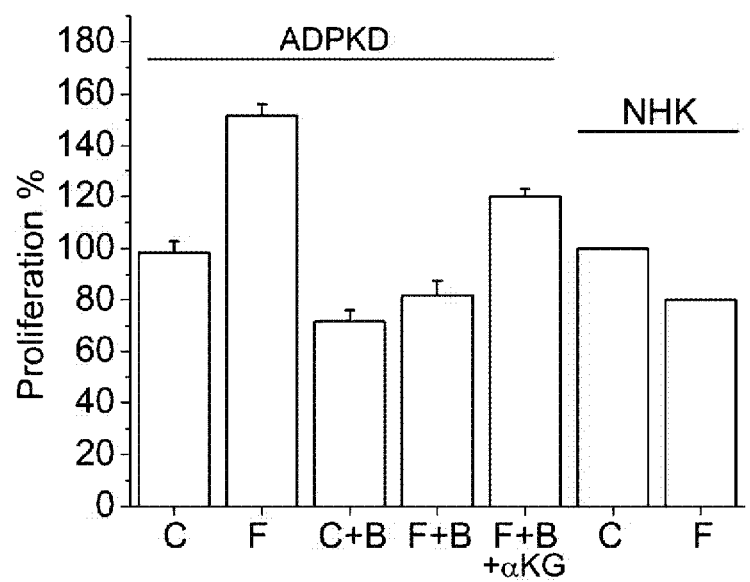
FIG. 9. BPTES inhibits proliferation stimulated with 8-bromo-cAMP which is rescued by dimethyl α-ketogutarate. ADPKD cells were stimulated with 8-bromo-cAMP (F) in the presence or absence of BPTES (B), or BPTES+ α-ketogutarate and proliferation was assessed by the MTT assay [performed in accordance with the manufacturer's (Promega's) instructions].

FIG. 9 shows that BPTES inhibits proliferation stimulated with 8-bromo-cAMP and treatment with dimethyl α-ketoglutarate can rescue this inhibition. To investigate whether BPTES inhibits cyst formation at least partially by interfering with the proliferation of ADPKD cells, proliferation was assessed following stimulation with 8-Br-cAMP. As shown in FIG. 9, 8-Br-cAMP stimulated proliferation of ADPKD cells and inhibited proliferation of NHK cells. These findings are consistent with previously reported findings (Yamaguchi et al. 2003, Kidney International 63:1983-1994). Treatment with BPTES (B) led to a significant decrease in proliferation of ADPKD cells (FIG. 9). The inhibition of proliferation by BPTES was specific, as demonstrated by the finding that addition of dimethyl, α-ketoglutarate, which functions downstream of Gls1, rescued the inhibition of proliferation. Although not shown herein, control NHK cells were inhibited by BPTES to a similar degree as ADPKD cells.

Figure 10:
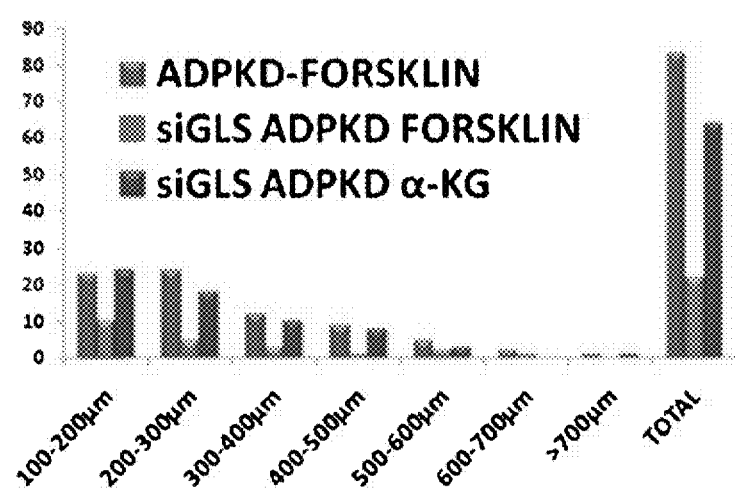
FIG. 10. siRNA to Gls1 inhibits cyst formation of ADPKD cells. ADPKD cells were transfected with a control or siRNA to Gls1 and cyst formation was assessed. Number of cysts in control (blue), siRNA transfected cells (green), or siRNA transfected cells cultured with dimethyl α-ketoglutarate (red).

FIG. 10 depicts results from experiments using siRNA to Gls1 to determine the effects of same on cyst formation of ADPKD cells. To confirm that BPTES inhibits growth of ADPKD cells by inhibiting Gls1, ADPKD cells were transfected with siRNA to Gls1 using lipofectamine, and cyst formation was assessed as shown in FIGS. 1 and 2. siRNA knockdown of Gls1 led to a statistically significant decrease in cyst formation (FIG. 10. compare blue and green). Inhibition was, moreover, specific as shown by addition of dimethyl α-ketoglutarate to the medium, which functions downstream of Gls1, and resulted in a statistically significant rescue of cyst formation in siRNA transfected cells (FIG. 10, red). The present inventors determined that siRNA expression resulted in about a 70-80% decrease in Gls1 protein and mRNA expression when quantitated relative to β-actin (shown on previous submission). The following are exemplary siRNA sequences used for inhibition of Gls1 atggtggtttctgcccaatta (SEQ ID NO: 1); SASI_Hs01_00071573-GAUGGAUUGUUGUAAUGGU [dT][dT] (SEQ ID NO: 2); 2260 NM_014905-ACCAUUA-CAACAAUCCAUC (SEQ ID NO: 3); SASI_Hs01_00071574-CAUUCUACUGGAGAUACCA [dT][dT] (SEQ ID NO: 4); 1081 NM_014905-UGGUAU-CUCCAGUAGAAUG (SEQ ID NO: 5).

Figure 11:
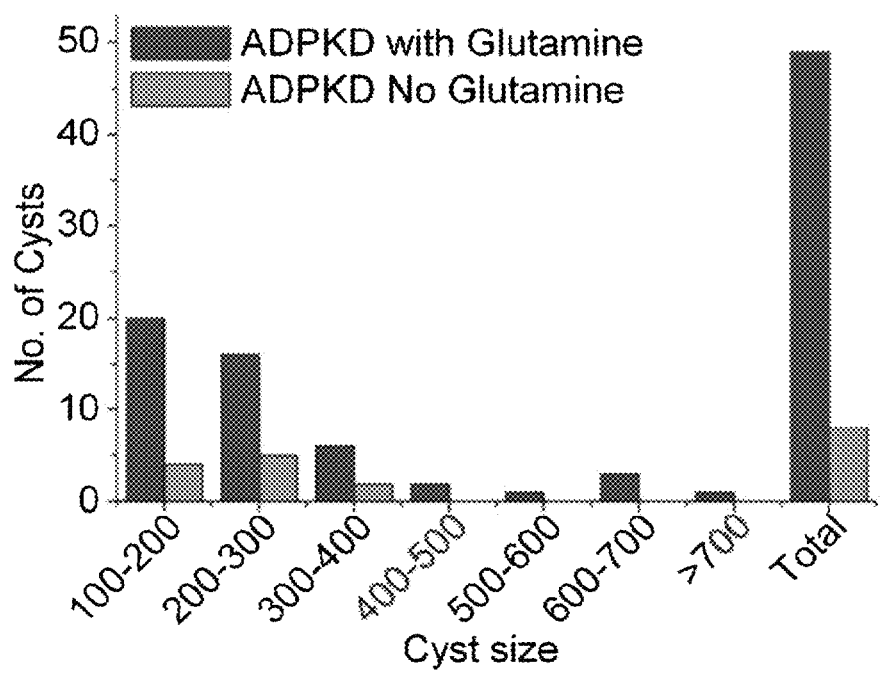
FIG. 11. ADPKD cells fail to form cysts in glutamine free media. Cyst formation of ADPKD cells was assessed in the presence or absence of glutamine. Total number of cysts were counted and stratified by cyst size.

FIG. 11 shows that ADPKD cyst formation is inhibited in glutamine free medium. The present inventors reasoned that if ADPKD cells require glutamine for proliferation, cyst formation should also be inhibited in glutamine free medium. FIG. 11 reveals that the presence of glutamine is, indeed, correlated with cyst formation in ADPKD cells.

FIG. 12 demonstrates that BPTES slows cyst growth in $PKD1^{flox/flox}$; Tamoxifen-Cre mice, an accepted animal model for ADPKD. Using an optimized dosing regimen, the present inventors evaluated BPTES in Tamoxifen-Cre mice treated with a high dose of BPTES (12.5 mg/kg IP BID). Cre recombinase was induced on postnatal day 10 by administering tamoxifen (10 mg/40 g) intraperitoneally (IP) on two consecutive days. Mice were then treated with BPTES or vehicle control starting on postnatal day 15 and continued until day 32, at which time mice were sacrificed and cyst growth assessed. Only same sexed mice from same litters were compared. These studies demonstrated the BPTES treatment led to a statistically significant inhibition of cyst growth (FIG. 12, N=4). There was no difference in body weight between control (16.14, SD 1.38) and BPTES (15.82, SD 1.40) treated animals.

FIG. 13 shows that blocking Gls1 inhibits ATP generation and mitochondrial respiration. The decreased generation of α-ketoglutarate, which feeds directly into tricarboxylic acid (TCA) would be predicted to lead to decreased TCA intermediates required for mitochondrial respiration and ATP generation. Seahorse analysis (Seahorse Biosciences) was performed on ADPKD cells that were either unstimulated or stimulated with forskolin in the presence or absence of BPTES. These studies demonstrated BPTES inhibited basal and forskolin stimulated ATP production and mitochondrial $O_2$ consumption. Forskolin also led to a statistically significant increase in maximal $O_2$ consumption.

Figure 14:
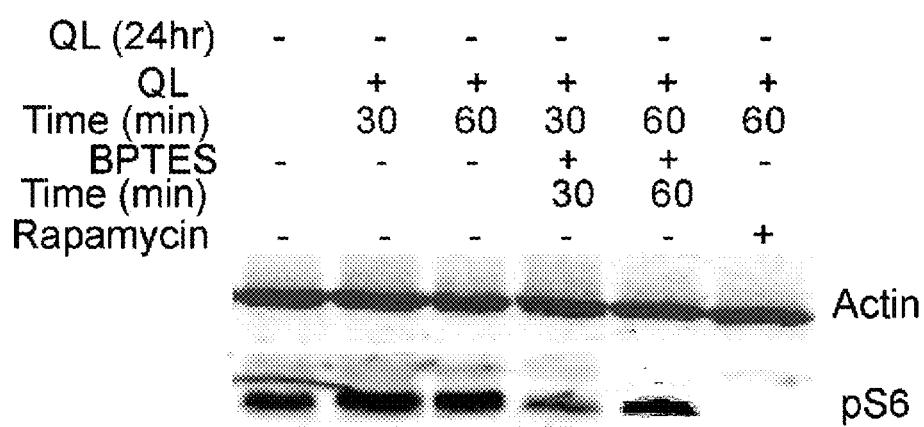
FIG. 14. BPTES inhibits mTor activation in ADPKD cells. Following deprivation of amino acids for 3 hours, ADPKD cells were refed with media containing glutamine (Q) and lysine (L) in the presence or absence of BPTES for 30 or 60 minutes. Cells were then lysed and mTOR activation was assessed by immunoblotting with anti-phospho-S6 antibodies (pS6). To control for loading, the same samples were immunoblotted with antibodies to actin (Actin).

FIG. 14 shows that blocking Gls1 inhibits mTOR activation. Amino acid activation of mTor is critical for cell growth. Moreover, inhibiting mTor has been proposed to be a good therapeutic target for treating ADPKD as treatment of rodent models of ADPKD with mTor inhibitors has been shown to slow cyst growth and preserve renal function (Duran et al. 2012, Molec Cell 47:349-358; Shillingford et al. 2006, Proc Natl Acad Sci 103:5466-5471; Tao et al. 2005, J Am Soc Nephrol 16:46-51; Gattone et al. 2009, Kidney Int 76:178-182; the entire content of each of which is incorporated herein by reference). Glutamine is metabolized though Gls1 to generate α-ketoglutarate which has been shown to mediate the activation of the mTor pathway (Duran et al. 2012, Molec Cell 47:349-358). The present finding that Gls1 inhibition also blocks mTor activation provides an additional mechanism whereby inhibiting Gls1 may slow cyst growth and provides further evidence that targeting Gls1 will simultaneously inhibit multiple signaling pathways involved in cyst growth.

FIG. 15 supports the findings of FIG. 14 and further demonstrates that inhibiting Gls1 blocks the recruitment of mTORC1 to the lysosome. The generation of α-ketoglutarate by glutamine metabolism has been shown to lead to GTP loading of RagB on the lysosome, which then recruits mTORC1 to the lysosome. The recruitment of mTORC1 to the lysosome is critical for its activation. Consistent with the findings of FIG. 14, the results presented in FIG. 15 reveal that inhibiting Gls1 inhibits mTor activation by blocking its recruitment to the lysosome.

In total, results presented herein demonstrate that gls1 plays a pivotal role in proliferation and cyst formation in ADPKD and establish gls1 as a novel therapeutic target for regimens designed to reduce the number and/or size of cysts in the kidneys of patients afflicted with ADPKD. Methods directed to administering gls1 inhibitors to treat human subjects afflicted with ADPKD are, therefore, envisioned and encompassed herein. Based on the results presented herein, such methods are predicted to confer symptomatic relief to ADPKD patients.

Therefore, if appearing herein, the following terms shall have the definitions set out below.

As used herein, the term "polycystic kidney disease" refers to a hereditary disorder characterized abnormal cellular proliferation, the growth of numerous fluid-filled cysts, remodeling of extracellular matrix, inflammation, and fibrosis in the kidney and liver.

The "subject" or "patient" afflicted with PKD treatable with the compounds/agents described herein can be any animal, and is preferably a mammal, such as a wild or domesticated animal or a livestock animal or a human.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Two amino acid sequences are "substantially homologous" when at least about 70% of the amino acid residues (preferably at least about 80%, and most preferably at least about 90 or 95%) are identical, or represent conservative substitutions.

The term "preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term "prophylaxis" is related to "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment, "treating" or "treatment" refers to ameliorating at least one physical parameter of the disease. In yet another embodiment, "treating" or "treatment" refers to modulating the disease or disorder, either physically, (e.g., stabilization of a discernible symptom), physiologically (e.g., stabilization of a physical parameter), or both. In a further embodiment, "treating" or "treatment" relates to slowing the progression of the disease. With respect to alleviating symptoms of PKD in a subject/patient, symptomatic relief would include, for example, a reduction in pain due to cystic engorgement of organs, particularly the kidneys, reduction in hypertension, and a reduction in the frequency of urinary tract infections.

The term "inhibit" or "inhibiting" refers to a statistically significant and measurable reduction in activity, preferably a reduction of at least about 10% versus control, more particularly a reduction of about 50% or more, still more particularly a reduction of about 80% or more. With respect to inhibiting ADPKD, the number of cysts and/or volume of the cysts due to the disease may be reduced by at least about 10%, at least about 20%, at least about 30%, at least about 40%, at least about 50%, at least about 60%, at least about 70%, at least about 80%, at least about 90%, at least about 95%, or about 100%.

A reduction in cyst volume and/or number following therapeutic intervention may be assessed using various visualization techniques known in the art, as well as an improvement in clinical symptoms. With regard to methods and devices used for visualizing cyst volume and/or number, trials are now underway that evaluate changes in cyst volume and total cyst volume using magnetic resonance imaging (MRI). The CRISP study and the Tolvaptan trial (tempo 3,4) present exemplary methods for assessing cyst volume using MRI. See, for example, Torres et al. 2012, The New England Journal of Medicine 367: 2407-2418 and Chapman. 2008, Clinical Journal of the American Society of Nephrology: CJASN, 3: 1197-1204; the entire content of each of which is incorporated herein by reference. In addition, renal function end points such as the reciprocal of the serum creatinine over time or time to doubling of serum creatinine may also be used to assess therapeutic response to an agent or compound administered for treating ADPKD.

Other meaningful clinical endpoints include, without limitation, a decreased incidence of significant abdominal discomfort/pain as reflected by fewer work absences and/or a reduced need for narcotics. Therapeutic efficacy may also be evaluated by assessing changes in hypertensiveness, wherein reduced hypertension indicates that the therapeutic intervention is achieving the desired objective of reducing kidney cyst volume and thereby improving kidney function. Yet another useful clinical endpoint involves interviewing the treated patient to determine if he/she is experiencing fewer symptoms and generally feels better.

The phrase "pharmaceutically acceptable" refers to molecular entities and compositions which are suitable for use in contact with the tissues of human beings and animals without excessive toxicity, irritation, allergic response, or other problem or complication, commensurate with a reasonable benefit/risk ratio.

A "therapeutically effective amount" is an amount of a compound or agent described herein or a combination of two or more such compounds, which inhibits, totally or partially, the progression of the condition or alleviates, at least partially, one or more symptoms of the condition. The amount that is therapeutically effective will depend upon the patient's size and gender, the condition to be treated, the severity of the condition and the result sought. For a given patient, a therapeutically effective amount can be determined by methods known to those of skill in the art.

With reference to the treatment of ADPKD using a compound or agent described herein, a "therapeutically effective amount" refers to that amount which has the effect of (1) reducing the size and/or number of the cysts, (2) slowing or inhibiting cyst growth or new cyst formation, and/or, (3) ameliorating one or more symptoms associated with the PKD, including extrarenal manifestations of the disease.

According to another aspect, the present invention provides a pharmaceutical composition, which comprises a therapeutically-effective amount of one or more compounds described herein or a pharmaceutically-acceptable salt, ester or prodrug thereof, together with a pharmaceutically-acceptable diluent or carrier.

The compositions may be formulated for any route of administration, in particular for oral, rectal, transdermal, subcutaneous, intravenous, intramuscular, intraperitoneal, or intranasal administration. The compositions may be formulated in any conventional form, for example, as tablets, capsules, caplets, solutions, suspensions, dispersions, syrups, sprays, gels, suppositories, patches and emulsions.

Systemic delivery is, for example, envisioned for siRNA, morpholinos, or antisense to glutaminase 1 mRNA. All of these agents can be delivered to the kidney in therapeutically effective amounts via systemic administration and work well in the kidney.

In a particular embodiment, a glutaminase inhibitor or composition thereof is administered systemically. In a more particular embodiment, the glutaminase inhibitor is an oral small molecule or a formulation thereof suitable for intravenous, subcutaneous, or intraperitoneal administration.

The compositions are administered in a manner compatible with the dosage formulation, and in a therapeutically effective amount. The quantity to be administered depends on the subject to be treated, capacity of the subject's immune system to utilize the active ingredient, and degree of inhibition or cell modulation desired. Precise amounts of active ingredient required to be administered depend on the judgment of the practitioner and are particular to each individual. However, suitable dosages may range from about 0.1 to 20, preferably about 0.5 to about 10, and more preferably one to several milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Methods comprise administering to the subject in need of such treatment an effective amount of one or more glutaminase 1 inhibitors described herein. Aspects also encompassed herein include use of one or more glutaminase 1 inhibitors for treating a subject in need thereof or in the preparation of a medicament for the treatment of a disease or condition, such as ADPKD.

A subject or patient in whom administration of the therapeutic compound is an effective therapeutic regimen for a disease or disorder is preferably a human, but can be any animal, including a laboratory animal in the context of a pre-clinical trial, including screening and/or activity assessment experiments. Thus, as can be readily appreciated by one of ordinary skill in the art, the methods, compounds and compositions described herein are particularly suited to administration to any animal suffering from ADPKD or an animal model thereof, particularly a mammal, and including, but by no means limited to, humans; domestic animals, such as feline or canine subjects, farm animals, such as but not limited to bovine, equine, caprine, ovine, and porcine subjects; research animals, such as mice, rats, rabbits, goats, sheep, pigs, dogs, cats, etc., and avian species, such as chickens, turkeys, songbirds, etc., i.e., for veterinary medical use.

Compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions.

In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are encompassed herein.

Compounds described herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference. Numerous standard references are, moreover, available that describe procedures for preparing various formulations suitable for administering the compounds described herein. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition), which are hereby incorporated by reference in their entirety.

Compounds described herein can also be administered in sustained release forms or from sustained release drug delivery systems. A description of representative sustained release materials can be found, for example, in *Remington's Pharmaceutical Sciences.*

The following formulation examples illustrate representative pharmaceutical compositions encompassed herein.

Compositions and methods described herein are not, however, limited to the following pharmaceutical compositions.

Formulation 1-Tablets

A compound described herein is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2-Capsules

A compound described herein is admixed as a dry powder with a starch diluent in an approximate 1:1 weight ratio. The mixture is filled into 250 mg capsules (125 mg of active amide compound per capsule).

Formulation 3-Liquid

A compound described herein (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4-Tablets

A compound described herein is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5-Injection

A compound described herein is dissolved or suspended in a buffered sterile saline injectable aqueous medium to a concentration of approximately 5 mg/ml.

Formulation 6-Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

METHODS OF TREATMENT

Compounds described herein are used as therapeutic agents for the treatment of ADPKD in vertebrates, and more particularly, mammals. Accordingly, the compounds and pharmaceutical compositions described herein find use as therapeutics for preventing and/or treating ADPKD in mammals, including humans.

The present inventors have shown that treatment of ADPKD cells with gls1 inhibitors reduces and/or blocks cyst formation in these cells. Indeed, treatment with an exemplary gls1 inhibitor, BPTES, dramatically reduced both the number and size of cysts in ADPKD cells. Inhibition of gls1 with BPTES also markedly decreased forskolin-induced proliferation of ADPKD cells. Results presented herein also reveal that glutamine is an important source of ATP in ADPKD cells. These results demonstrate that gls1 plays a pivotal role in proliferation and cyst formation in ADPKD. In keeping with this evidence, the present inventors advocate methods for treating subjects afflicted with ADPKD, wherein such methods call for administering therapeutically effective amounts of gls1 inhibitors to these subjects so as to slow cyst growth and progression to end stage kidney disease in subjects with ADPKD.

Further to the above, in a method of treatment aspect, a method of treating a mammal susceptible to or afflicted with ADPKD is envisioned, which method comprises administering an effective amount of one or more of the pharmaceutical compositions just described. Such methods comprise administering an effective condition-treating or condition-preventing amount of one or more of the pharmaceutical compositions just described.

As a further aspect, the present compounds are set forth for use as a pharmaceutical, especially in the treatment or prevention of ADPKD. Also provided herein is the use of the present compounds in the manufacture of a medicament for the treatment or prevention of ADPKD.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of ADPKD, the regimen for treatment usually stretches over many months or years, so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with particular doses each providing from about 0.1 to about 10 mg/kg and especially about 1 to about 5 mg/kg.

Exact dosing of a compound described herein will depend on bioavailability of the compound and the route of delivery. BPTES, for example, can be administered at 25 mg/kg twice a day. More water soluble gls1 inhibitors, including more water soluble BPTES analogs, may, for example, be administered orally at 50 mg/kg, 100 mg/kg, 150 mg/kg, 200 mg/kg, or 250 mg/kg twice a day.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa. One of skill in the art would choose an appropriate delivery mode/s based on a variety of parameters, including the organ or tissue site in a patient with a disease or condition that is most severely affected by the disease or condition. A skilled practitioner could, for example, treat a patient afflicted with ADPKD with a therapeutic regimen that included delivery of the compounds or compositions described herein using some means for direct delivery to the kidneys.

When used to prevent the onset of ADPKD, the compounds described herein will be administered to a patient at risk for developing ADPKD, typically on the advice and under the supervision of a physician, at the dosage levels described above. Patients at risk for developing a particular condition generally include those that have a family history of the condition, or those who have been identified by genetic testing or screening to be particularly susceptible to developing the condition.

It is also envisioned that a subject/patient with ADPKD may be evaluated to determine if he/she is a good candidate for a treatment regimen presented herein. Such evaluations would involve an assessment of gls1 activity in the kidneys of the patient, which may be performed using standard assays. Assays are known to those skilled in the art and include analysis of kidney function by analysis of, for example, urine or blood samples; or biopsy of kidney tissue followed by immunohistochemistry.

Compounds described herein can be administered as the sole active agent or they can be administered in combination with other agents, including other compounds that demonstrate the same or a similar therapeutic activity and are determined to safe and efficacious for such combined administration.

Other compounds/agents that are envisioned for use in combination with gls1 inhibitors (e.g., BPTES and analogs thereof) include: HDAC inhibitors (U.S. Application Ser. No. 2012/0122787; Cao et al. 2009, Proc Natl Acad Sci 106: 21819-24; the entire content of which is incorporated herein by reference); Src inhibitors (Sweeney et al. 2008, J Am Soc Nephrol. 19(7):1331-1341; the entire content of which is incorporated herein by reference); Sirtuin 1 inhibitors (Zhou et al. 2013, J Clin Invest. 123(7):3084-3098; the entire content of which is incorporated herein by reference); Tumor necrosis factor inhibitors (Li et al. 2008, Nat Med 14:863-868; the entire content of which is incorporated herein by reference); Epidermal growth factor and receptor inhibitors (Sweeney et al. 2000, Kidney Int. 57(1):33-40; the entire content of which is incorporated herein by reference); HER2 inhibitors (Wilson et al. 2006, Biochim Biophys Acta 1762(7):647-55; the entire content of which is incorporated herein by reference); Braf inhibitors (Yamaguchi et al. 2010, Am J Physiol Renal Physiol. 299(5):F944-F951; the entire content of which is incorporated herein by reference); and inhibitors of hepatocyte growth factor and its receptor cMET (Qin et al. 2012, J Am Soc Nephrol. 23(8):1309-1318; the entire content of which is incorporated herein by reference).

Glutaminase Inhibitors

The term "glutaminase inhibitor" as used herein refers to inhibitors that reduce the activity of the glutaminase enzyme, such as inhibitors that may affect binding of glutamine, glutamate or various cofactors to the enzyme. A glutaminase inhibitor may, therefore, block binding of the substrate glutamine to glutaminase, inhibit release of the product glutamate from glutaminase, or block cofactor binding and therefore slow the catalytic rate of the enzyme. Exemplary inhibitors of glutaminase activity which may be utilized in methods, uses, and medicaments described herein include 6-diazo-5-oxo-L-norleucine (DON); N-ethylmaleimide (NEM); p-chloromercuriphenylsulfonate (pCMPS); L-2-amino-4-oxo-5-chloropentoic acid; DON plus o-carbamoyl-L-serine; acivicin [(alphaS,5S)-alpha-amino-3-chloro-4,5-dihydro-5-isoxazoleacetic acid]; azaserine; 5-(3-bromo-4-(dimethylamino)phenyl)-2,2-dimethyl-2,3,5,6-tetrahydrobenzo[-a]phenanthridin-4(1H)-one; and small molecule inhibitors of glutaminase, such as, for example, a compound of Formula (I); and combinations or derivatives thereof or pharmaceutically acceptable salts thereof.

In a particular embodiment thereof, the inhibitor of glutaminase is selected from the group consisting of a compound of Formula (I):

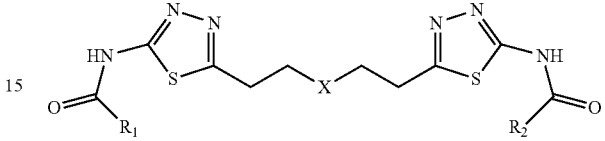

wherein: X is sulfur or oxygen; $R_1$ and $R_2$ are independently selected from the group consisting of lower alkyl, lower alkoxyl, aryl, thiophenyl and $—(CH_2)_n$-aryl; wherein n is 0 or 1, and aryl is a monocyclic aromatic or heteroaromatic group, having ring atoms selected from the group consisting of carbon, nitrogen, oxygen, and sulfur, and having at most three non-carbon ring atoms, which group may be unsubstituted or substituted with one or more substituents selected from the group consisting of halogen, lower alkyl, lower alkoxyl, amino, lower alkyl amino, amino(lower alkyl), or halo(lower alkyl). In a particular embodiment, the compound of Formula (I) is bis-2-(5-phenylacetamido-1,2,4-thiadiazol-2-yl)ethyl (BPTES).

Representative compounds of Formula (I) comprise compounds such as those disclosed in U.S. Pat. No. 6,451,828 and U.S. Patent Application No. (U.S.) 2013/0109643, the entire content of each of which is incorporated herein by reference. In a particular embodiment of Formula (I), X is sulfur. In further particular embodiments, each of $R_1$ and $R_2$ is selected from the group consisting of $—(CH_2)_n$-aryl, 2-thiophenyl, 2-furanyl, phenyl or benzyl, unsubstituted or substituted with lower alkyl or lower alkoxyl, benzyl, p-methoxy phenyl, $R_1$ and $R_2$ is m-tolyl, lower alkoxyl, ethoxy, lower alkyl, and t-butyl. In a particular embodiment, the compound of Formula (I) is bis-2-(5-phenylacetamido-1,2,4-thiadiazol-2-yl)ethyl sulfide (BPTES):

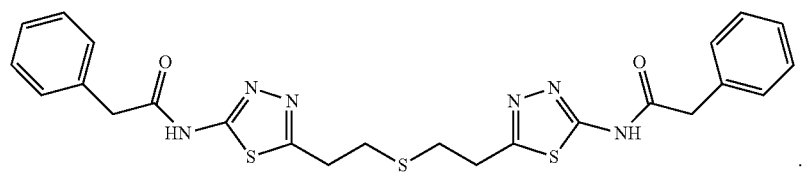 [SMILES: O=C(Cc1ccccc1)Nc1nnc(CCSCCc2nnc(NC(=O)Cc3ccccc3)s2)s1]

Further to the above, DeLaBarre et al. (Biochemistry (50) 2011:10764-70) have determined the crystal structure of BPTES complexed to GLS1. This structure revealed that two BPTES molecules bind at an interface region where two GLS1 dimers combine to form a tetramer, thereby locking GLS1 in a nonproductive conformation and inhibiting its enzymatic activity. BPTES is the prototype for a specific GLS1 inhibitor and has, moreover, served as the starting point for chemists to design and make new GLS1 inhibitors that are based on the BPTES backbone structure. These new GLS1 inhibitors are, therefore, referred to as analogs of BPTES. See, for example, Shukla et al. (2012, J Med Chem 55:10551-63), the entire content of which is incorporated herein by reference. As described in greater detail herein below and in Shukla et al. (supra), the overall goal of these investigators has been to chemically modify BPTES to make a variety of new GLS1 inhibitors that have better pharmacologic properties. The Shukla et al. reference, for example, describes the generation of BPTES analogs that still maintain the ability to inhibit GLS1, but have improved water solubility and, therefore, may have superior pharmaceutical properties relative to BPTES. Methods for treating a subject afflicted with ADPKD using such BPTES analogs are, therefore, envisioned herein.

Another GLS1 inhibitor, the bromo-phenanthridinone molecule 968, is a second class of GLS1 inhibitors, that was identified in a screen designed to look for inhibitors of Rho-dependent transformation. 968 was subsequently shown by Wang et al. (Cancer Cell. 2010 Sep. 14; 18(3): 207-219. doi:10.1016/j.ccr.2010.08.009) to inhibit GLS1. As yet, 968 has not been crystallized with GLS1, so the exact mechanism whereby 968 inhibits GLS1 has not as yet been determined. Nevertheless, 968 works differently than BPTES as it only inhibits the nonactivated dimeric GLS1 and not the active tetramer. This is consistent with BPTES, but not 968, being able to inhibit phosphate-activated GLS1. See, for example, Wang et al. (Cancer Cell. 2010 Sep. 14; 18(3): 207-219. doi:10.1016/j.ccr.2010.08.009) and Katt et al. (Mol Cancer Ther. 2012 June; 11(6): 1269-1278. doi: 10.1158/1535-7163.MCT-11-0942). 968 has poor aqueous solubility and therefore most experiments to date have been performed in vitro and not in animals. Nevertheless, it is anticipated that analogs of 968 will be developed in the future that have better pharmacologic properties and such compounds are envisioned herein.

The term "glutaminase inhibitor" will also be understood to include specific inhibitors of glutaminase production. Inhibitors of glutaminase production, therefore, include specific inhibitors of transcription of the gene encoding glutaminase. Such inhibitors include siRNA and similar RNA-based molecules with sequence specificity for glutaminase RNA (including morpholinos), which specifically inhibit glutaminase transcription. The term "glutaminase inhibitor" may, therefore, be used to refer to agents that specifically target and inhibit glutaminase transcription and do not, for example, inhibit glutaminase transcription indirectly via modulation of other cellular proteins (e.g., c-myc) or cellular pathways associated therewith that are generally associated with cellular transformation.

With respect to compounds of Formula (I), the terms below have the following meanings unless indicated otherwise.

"Alkyl" refers to a fully saturated acyclic monovalent radical containing carbon and hydrogen, which may be branched or a straight chain. Examples of alkyl groups are methyl, ethyl, n-butyl, n-heptyl, and isopropyl. "Lower alkyl," a subset of this class, refers to alkyl having one to six carbon atoms, and more preferably one to four carbon atoms.

"Aralkyl" refers to a monovalent alkyl radical substituted with an aryl group, as defined herein, e.g. a benzyl group ($—CH_2C_6H_5$).

As used herein, "aryl" refers to a monocyclic aromatic or heteroaromatic group, having ring atoms selected from the group consisting of carbon, nitrogen, oxygen, and sulfur, and having at most three non-carbon ring atoms. The aryl group may be unsubstituted, or it may be substituted with one or more substituents selected from halogen, lower alkyl, lower alkoxy, amino, lower alkyl amino, amino(lower alkyl), and halo(lower alkyl). Preferably, each ring has at most three substituents, more preferably at most two, and most preferably one or no substituents.

A "pharmaceutically acceptable salt" of a compound described herein refers to the compound in protonated form with one or more anionic counterions, such as chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like. Hydrochloride salts are a preferred group. The term also encompasses carboxylate salts having organic and inorganic cations, such as alkali and alkaline earth metal cations (for example, lithium, sodium, potassium, magnesium, barium and calcium); ammonium; or organic cations, for example, dibenzylammonium, benzylammonium, 2-hydroxyethylammonium, bis(2-hydroxyethyl) ammonium, phenylethylbenzylammonium, dibenzylethylenediammonium, and the like. Such salts may be formed by substitution of ionizable groups onto, for example, phenyl rings in group $R_1$ or $R_2$, which can be useful for increasing solubility or for reducing membrane permeability, if desired.

The compounds described herein may exist in other forms depending on solvent, pH, temperature, and other variables known to practitioners skilled in the art. For example, equilibrium forms may include tautomeric forms. The compounds may be chemically modified to enhance specific biological properties, such as biological penetration, solubility, oral availability, stability, metabolism, or excretion. The compounds may also be modified to prodrug forms, such that the active moiety results from the action of metabolic or biochemical processes on the prodrug.

As alluded to herein above, additional exemplary glutaminase inhibitors are also described in U.S. 2012/0220610; Wang et al. (Cancer Cell. 2010 Sep. 14; 18(3): 207-219. doi:10.1016/j.ccr.2010.08.009); Katt et al. (Mol Cancer Ther. 2012 June; 11(6): 1269-1278. doi:10.1158/1535-7163.MCT-11-0942); Shukla et al. (2012, J Med Chem 55:10551-63); and U.S. Pat. No. 7,714,007, the entire content of each of which is incorporated herein by reference.

Shukla et al. (supra), for example, describe studies designed to identify BPTES analogs having improved drug-like molecular properties. Their structure-activity relationship (SAR) studies revealed that some truncated analogs retain the potency of BPTES, which may provide compounds possessing improved aqueous solubility. One of the analogs, N-(5-{2-[2-(5-amino-[1,3,4]thiadiazol-2-yl)-ethylsulfanyl]-ethyl}-[1,3,4]thiadiazol-2-yl)-2-phenyl-acetamide (compound 6) exhibited similar potency and better solubility relative to BPTES and attenuated the growth of P493 human lymphoma B cells in vitro and in a mouse xenograft model. Accordingly, BPTES analogs described by Shukla et al. are envisioned as exemplary glutaminase inhibitors useful in methods, uses, and the preparation of medicaments as described herein.

Additional chemical analogs of BPTES are described in U.S. Pat. No. 8,604,016 and Gross et al. (2014, Mol Cancer Ther 13:890-901), the entire content of each of which is incorporated herein by reference. Accordingly, BPTES analogs described in U.S. Pat. No. 8,604,016 and Gross et al. are envisioned as exemplary glutaminase inhibitors useful in methods, uses, and the preparation of medicaments as described herein.

U.S. 2012/0220610, Wang et al., and Katt et al., for example, describe a dibenzophenanthridine, 5-(3-bromo-4-(dimethylamino)phenyl)-2,2-dimethyl-2,3,5,6-tetrahydrobenzo[a]phenanthridin-4(1H)-one, designated 968, which has been identified as a glutaminase specific inhibitor. The entire content of U.S. 2012/0220610, Wang et al., and Katt et al. are incorporated herein by reference. The structure of small molecule 968 is shown below as indicated, alongside derivatives thereof as described in Katt et al.:

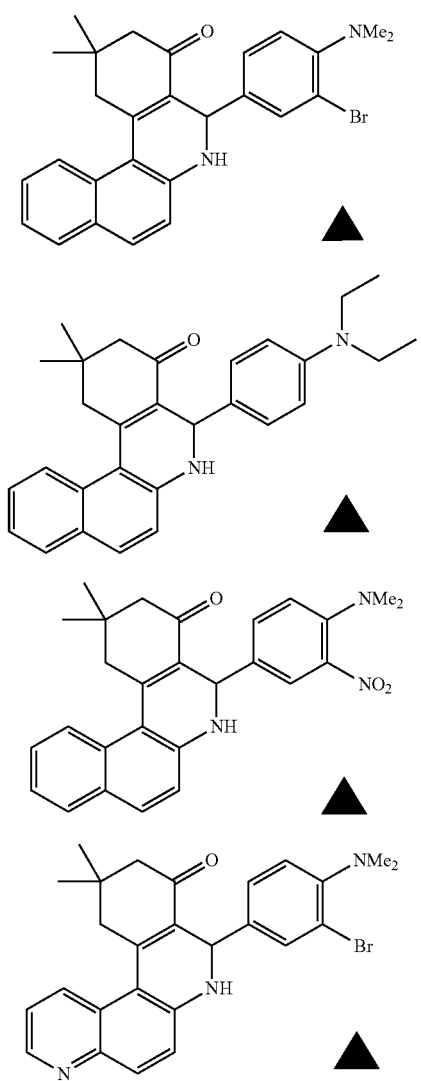

Additional derivatives of small molecule 968 are also described in, for example, Katt et al. Those derivatives which act as glutaminase inhibitors are also encompassed herein for use in methods for treating ADPKD. Compound 968 (i.e., small molecule 968) is available from commercial vendors, including Calbiochem.

Further to the above, WO2013/078123 describes heterocyclic inhibitors of glutaminase for use in treating, for example, cancer. The entire content of WO2013/078123 is incorporated herein by reference.

BPTES is set forth herein as an exemplary glutaminase inhibitor. Underscoring its utility in methods for treating ADPKD, BPTES confers significant reduction in kidney size and cyst volume in animal models of ADPKD. As described herein, an exemplary dosing regimen for BPTES in mice is 12.5 mg/kg, administered intraperitoneally, twice a day (BID). See, for example, FIGS. 6 and 12.

It will be appreciated, however, that more water soluble forms of gls1 inhibitors may be administered orally. Suitable dosing parameters for more water soluble gls1 inhibitors may be determined empirically, but may range from 1-500 mg/kg administered orally (via, for example, oral gavage for mice) twice a day. More particularly, the dosing may range from 1-400 mg/kg, 1-300 mg/kg, 1-250 mg/kg, 1-200 mg/kg, 1-150 mg/kg, 1-100 mg/kg, or 1-50 mg/kg administered orally, twice a day in mice.

Compounds described herein may be purchased from various commercial sources or can be prepared from readily available starting materials using the following general methods and procedures. BPTES (CAS Number 314045-39-1), for example, can be purchased from Sigma-Aldrich (see the Sigma-Aldrich website on the worldwide web, catalog # SML0601 It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Synthesis of BPTES and Derivatives Thereof

BPTES and related compounds, including analogs, may be synthesized in accordance with the protocols set forth in U.S. Pat. No. 6,451,828 and Thangavelu et al. 2012, Proc Natl Acad Sci 109:7705-7710, the entire content of each of which is incorporated herein in its entirety.

In accordance with U.S. Pat. No. 6,451,828, BPTES can be synthesized by adding 9.1 g thiosemicarbazide ($H_2N$(C=S)$NHNH_2$), 8.9 g 3,3'-thiodipropionic acid (see FIG. 1), and 90 mL $POCl_3$ into a pear-shaped flask. The resulting suspension is then heated at 90° C. for 3 h, then cooled to room temperature and poured into 400 g of ice. The resulting mixture is filtered and then brought to pH 14. The white solid which formed is washed with 2×200 mL water and dried in vacuo at 50° C. to give 8 g bis-2'-(5-amino-1,3,4 thiadiazol-2-yl)ethyl sulfide. This product (4.32 g) is heated with 24 mL pyridine and 4.5 mL phenyl acetyl chloride until the mixture was homogeneous. The solution is cooled to room temperature and triturated with 50 mL methanol and filtered to give a crude solid. This solid is redissolved in 8 mL DMSO, 50 mL methanol added, and the solution allowed to sit at room temperature as the product crystallizes. The product is collected and dried in vacuo at 50° C. to give approx. 1.5 g of the product.

BPTES and derivatives thereof can be synthesized in accordance with protocols set forth in Thangavelu et al. Compounds synthesized therein are referred to as follows: Bis-2'-[5-amino-1,3,4-thiazol-2-yl]ethylsulfide (1); 1,5-(5-amino-1,3,4-thiadiazol-2yl)pentane (2); 1,5-(5-amino-1,3,4-thiadiazol-2yl)butane (3); Bis-2'-[5-(phenylacetamido)-1,3,4-thiazol-2-yl]ethylsulfide (4); and Bis-2'-[5-(3,4,5-trimethoxybenzamido)-1,3,4-thiadiazol-2-yl]ethyl sulfide (5). Diamino compounds (2-4) are prepared by refluxing thiosemicarbazide (5 mmol) and appropriate dicarboxylic acid (15 mmol) in the presence of POCl3 for 2 h. Upon cooling, the reaction mixture is poured over 200 g of ice. The turbid suspension is filtered, and the filtrate basified with potassium carbonate to precipitate the product. The precipitate is filtered and washed with copious amounts of water and dried at vacuum to afford the target amines in moderate yield of ≈50%. The amide derivatives (1 and 5) are synthesized by condensing the diamino compound (1) (1 mmol) and corresponding acid chloride (3 mmol) in dry pyridine for 12 h. After cooling, the reaction mixture is poured into 50 mL of methanol. The precipitated product is filtered and washed with plenty of methanol to afford the target compounds. General procedure for the synthesis of diamino bis-thiazole derivatives (1-3): thiosemicarbazide (0.45 g, 5 mmol) and appropriate dicarboxylic acid (15 mmol) are refluxed in 10 mL of POCl3 for 2 h. Upon cooling the reaction mixture is poured over 200 g of ice. The turbid suspension is filtered, and the filtrate basified with potassium carbonate to precipitate the product. The precipitate is filtered and washed with plenty of water and dried at vacuum. General procedure for amide synthesis (4 and 5): diamino compound 1 (1 mmol) and corresponding acid chloride (3 mmol) are refluxed in 10 mL of dry pyridine for 12 h. Upon cooling, the reaction mixture is poured into 50 mL of methanol. The precipitated product is filtered and washed with plenty of methanol to afford the target compound.

Animal Model Systems of ADPKD

There are two major types of PKD animal models: spontaneous hereditary models in which symptoms characteristic of PKD manifest and modified models established by mutation of human orthologous genes. These models are useful for identifying therapeutic agents, assessing therapeutic agents identified in in vitro assays, establishing therapeutic regimens, and determining/evaluating endogenous or exogenous factors related to disease progression.

Spontaneous hereditary models of PKD include: Han: SPRD-Cy (Cy) rats; Pcy mice; Jck mice; cpk (congenital polycystic kidney) and bpk (BALB/c polycystic kidney) mice. See, for example, Nagao et al. 2012, Exp Anim 61(5); 477-488 for a review and references cited therein.

Gene-modified models generated by mutation of human orthologous genes include: transgenic mice with increased expression of the human orthologous PKD1 gene; gene targeting mice for Pkd1 wherein human orthologous PKD genes, PKD1 and PKD2 are deleted; and Pkd2 gene targeting in mice. The Pkd2WS25/− mouse, which has an unstable allele, is viewed as one of the important animal models used for drug treatment studies because it has cysts in both the kidney and liver, and thus recapitulates features of human ADPKD patients. See, for example, Wu et al. 2000. *Nat. Genet.* 24:75-78, the entire content of which is incorporated herein by reference. This strain was established by crossbreeding of Pkd2+/− and Pkd2WS25/+. In Pkd2WS25/− mice, the weight (% of body weight) of the kidney and liver is 2-fold heavier as compared with that of wild-type mice. The rates of proliferation and apoptosis in epithelial cells of either renal cysts or cystic cholangiocytes are upregulated compared with those in normal tissues. See, for example, Stroope et al. 2010. *Am. J. Pathol.* 176: 1282-1291; and Nagao et al. 2012, Exp Anim 61(5); 477-488 for a review and references cited therein.

Exemplary animal models of ADPKD include a conditional knockout of PKD1 using a KSP-Cre to specifically delete PKD1 in renal tubular cells (Takiar et al. 2011, *Proc Natl Acad Sci USA*, 108: 2462-2467) and mice in which inducible deletion of PKD1 is achieved using a tamoxifen-Cre model (Piontek et al. 2007, *Nat Med*, 13: 1490-1495). The entire content of each of Takiar et al. and Piontek et al. is incorporated herein by reference. As described in Takiar et al., the most aggressive viable murine model of PKD is Pkd1 flox/−; Ksp-Cre, wherein renal cystic disease manifests within the first week of life and death occurs between the second and third weeks of life. See also Shibazaki et al. 2008, Hum Mol Genet 17:1505-1516, the entire content of which is incorporated herein by reference. Also described in Takiar et al. is an inducible model for Pkd1 inactivation, wherein a conditional Pkd1flox allele is used in combination with a tamoxifen-inducible Cre recombinase (pCX-CreER). See also Guo et al. 2002, Genesis 32:8-18; and Miyazaki et al. 1989, Gene 79:269-277. Induction of Cre expression before P13 leads to rapidly progressive cystic disease in Pkd1flox/flox animals. This animal model system of ADPKD is also described in Piontek et al. 2007, Nat Med 13:1490-1495.

As described in Karihaloo et al. (2011, J Am Soc Nephrol 22: 1809-1814), Pkd1$^{fl/fl}$; Pkhd1-Cre mice may be generated by crossing Pkd1fl/fl mice with Pkhd1-Cre mice13 so as to achieve kidney-specific deletion of the Pkd1 allele. See also Shibazaki et al. (2008, Hum Mol Genet 17, 1505-1516) and Patel et al. (2008, Hum Mol Genet 17, 1578-1590). The entire content of each of Karihaloo et al., Shibazaki et al., and Patel et al. is incorporated herein by reference.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

The present inventors have made the surprising discovery that inhibiting glutaminase 1 (gls1) blocks cyst formation and proliferation by ADPKD cells. As shown in FIGS. 1 and 2, inhibition of gls1 blocks cyst formation in vitro. ADPKD cells were plated in collagen and stimulated with the cyclic 3'-5'-adenosine monophosphate (cAMP) agonist forskolin. Cells were then cultured for 2 weeks in the presence or absence of the gls1 inhibitor BPTES bis-2-(5-phenylacetamido-1,2,4-thiadiazol-2-yl)ethyl sulfide and subsequently visualized. As depicted in FIG. 1, cysts were dramatically reduced in size and numbers responsive to BPTES treatment. The results are depicted graphically in FIG. 2, wherein the data were stratified according to both the number of observable cysts and their size. FIG. 2 shows that BPTES treatment markedly reduces the number of cysts and profoundly decreases the size of those cysts that are formed.

Elevated intracellular concentration of cAMP is characteristic of ADPKD cells in vivo and mediates activation of signaling pathways that lead to proliferation of ADPKD cells. Gls1 is also critical for proliferation of ADPKD cells. As shown in FIG. 3, the present inventors found that inhibition of gls1 with BPTES markedly decreased forskolin-induced proliferation of ADPKD cells. The decrease in proliferation of ADPKD cells by BPTES is due to gls1 inhibition and is not due to the nonspecific inhibition of another signaling pathway; co-culture of ADPKD cells with α-ketoglutarate reversed the inhibition of proliferation by BPTES. α-ketoglutarate is generated from the metabolism of glutamine by gls1 and ultimately mediates many of the pro-growth effects of glutamine on cells. Thus, the present finding that α-ketoglutarate rescues BPTES inhibition indicates BPTES inhibits ADPKD proliferation via its effects on gls1.

Consistent with gls1 being important for proliferation of ADPKD cells, the present inventors found that gls1 protein was markedly up-regulated in ADPKD cells following forskolin stimulation. Gls1 exists in 2 isoforms depending on whether exon 14 is spliced to exon 15 (GAC isoform) or whether exon 14 is spliced directly to exon 16 (KGA isoform). See, see FIG. 4. Protein expression of both gls1 isoforms was markedly up-regulated in ADPKD cells following forskolin stimulation. While both gls1 isoforms were also up-regulated in NHK cells, the percent increase was markedly decreased when compared with ADPKD cells (FIG. 4).

α-ketoglutarate also feeds directly into the tricarboxylic acid (TCA) cycle and therefore metabolism of α-ketoglutarate is an important source of ATP from glutamine. Consistent with glutamine also being an important source for ATP in ADPKD cells, the present inventors found that treatment of ADPKD cells with BPTES resulted in a significant decrease in intracellular ATP levels in ADPKD cells. These results indicate that ADPKD cells are sensitive to the effects of BPTES and thus, suggest that ADPKD can be targeted using BPTES and analogs thereof.

Further to the above, the ADPKD cells are pools of primary cells (PC) isolated from cyst lining epithelia. The NHK cells are a mixed population of PC isolated from nephrectomy specimens. Both stain primarily for *Dolichos biflorus* agglutinin indicating they are mostly distal tubule/ CD cells which is the origin of more that 70% of cysts in ADPKD (Yamaguchi et al. 2006, J Am Soc Nephrol 17:178-187; Yamaguchi et al. 2003, Kidney International 63:1983-19940. In contrast to NHK cells, ADPKD cells lack the polycystin protein which is mutated in ADPKD. In addition, ADPKD cells behave like ADPKD cells in vivo. In contrast to NHK cells whose proliferation is inhibited by cAMP agonist, ADPDK cell proliferation is stimulated by cAMP agonists. ADPKD cells also fail to increase calcium influx via polycystin 2, whereas calcium influx is normal in NHK cells. In light of the above, specific targeting of ADPKD cells in vivo may be facilitated by their differential expression of various cellular proteins and distinct metabolic properties.

These findings indicate that gls1 plays a pivotal role in proliferation and cyst formation in ADPKD and establish gls1 as a suitable target for intervention for the treatment of ADPKD. To explore further the potential for using gls1 inhibitors as agents for treating ADPKD, the present inventors have used animal model systems of ADPKD to evaluate efficacy in vivo. Suitable animal model systems are described below.

A number of animal model systems for ADPKD in humans are known. Conditional deletion of PKD1 in mice after post-natal day 14, when active proliferation in the developing kidney ceases, results in a disease that progresses more slowly and may more closely resemble disease in people. Inactivation of PKD1 in renal epithelia prior to postnatal day 13 via tamoxifen-inducible Cre, however, results in severe and explosive cystic disease (resembling Pkhd-Cre mice). Accordingly, inactivation of PKD1 after postnatal day 14 may provide a model system that more closely parallels that of human ADPKD because cyst formation occurs much more slowly in this context (Piontek et al., 2007, Nature medicine, 13: 1490-1495). Early and late models are described in greater detail herein below.

Experimental Design:

Early Models. PKD1$^{flox/flox}$; Tamoxifen-Cre Mice: The present inventors obtained the tamoxifen-Cre mouse model from G. Germino. For early onset disease, Cre recombinase is induced at day 10 by administering tamoxifen (10 mg/40 g) intraperitoneally (IP) on 2 consecutive days as described in FIG. 12 above and in Piontek et al. (2007, Nature medicine, 13: 1490-1495; the entire content of which is incorporated herein by reference). As described herein above, FIG. 12 presents results demonstrating that treatment with a Gls1 inhibitor, BPTES, slows cyst progression.

Pkhd-Cre Mice: This is a very robust and reproducible early model of PKD. The Somlo lab has shown that Pkhd-cre expresses and deletes predominantly in collecting tubules Ma et al. (2013, Nature genetics, 45: 1004-1012; the entire content of which is incorporated herein by reference). This animal model was used to generate the results presented in FIG. 6. As described herein, FIG. 6 shows that treatment with a Gls1 inhibitor, BPTES, slows cyst progression.

(ii) Late Model. Pax8rt; TetO-cre: The Pax8rtTA; TetO-cre doxycycline-inducible system also offers an excellent animal model system, which benefits from the feature that it is largely restricted to the nephron thus, parallels features of ADPKD in humans. The present inventors obtained these mice from S. Somlo (Ma et al., 2013, Nature genetics, 45: 1004-1012), have rederived them, and are now expanding the colony. Pax8; TetO-cre mice will be induced with 2 mg/kg doxycycline in the drinking water for two weeks starting on post-natal day 28.

Treatment: As discussed with respect to FIG. 12, the present inventors have spent a considerable amount of time identifying the best treatment regimen to inhibit Gls1 and glutaminolysis. We will perform experiments with BPTES, BPTES analogs, and other gls1 inhibitors known to skilled practitioners and described herein. For the pkhd-Cre mice, treatment will start on postnatal day 10 and mice will be sacrificed on day 28 in accordance with Ma et al. (2013, Nature genetics, 45: 1004-1012). Tamoxifen-Cre mice will be treated as described in FIG. 12. In addition, survival studies in both models will be performed to determine whether treatment with a Gls1 inhibitor prolongs survival by slowing cyst growth and preserving renal function. Pax8rt; TetO-cre mice will be treated following doxycycline induction and analyzed after 8-14 weeks as described (Ma et al., 2013, Nature genetics, 45: 1004-1012).

In addition to assessing inhibition of Gls1 in the kidney, plasma BPTES concentrations in serum and kidney will also be measured.

Histology: As described herein above, kidneys and animals will be weighed using routine methods, and the ratio of kidney weight/body weight calculated. Animals with bigger cysts should have a higher kidney/body weight ratio. Kidneys will be sectioned, stained by H&E, and cyst volume and kidney wt/body wt will be calculated as described and shown in FIG. 12 (Ma et al., 2013, Nature genetics, 45: 1004-1012). Mice will also be followed noninvasively by sonography to assess cyst growth over time to help identify the best time to sacrifice animals, particularly in Pax8rt mice.

Kidney Function: Renal function will be measured by assessing BUN and creatinine. For late onset disease, BUN and creatinine will be measured at monthly intervals and for early onset disease, prior to sacrifice. In the present inventors' experience, serum creatinine has not been a good marker for renal function as it is extremely low in normal mice and rises only modestly, even when the BUN increases 3-4× over baseline. The Somlo laboratory has shown a very good correlation between cyst volume and BUN (Ma et al., 2013, Nature genetics, 45: 1004-1012); therefore BUN will be the predominant measurement of kidney function utilized. We will also determine whether a Gls1 inhibitor prolongs survival in both models.

Proliferation and Apoptosis: Increased proliferation and apoptosis have been described in ADPKD (Takiar et al. Proc Natl Acad Sci USA, 108: 2462-2467, 2011; Shillingford et al. 2006, Proc Natl Acad Sci 103:5466-5471; the entire content of each of which is incorporated herein by reference), although some data has called these findings into question (Piontek et al. Nature medicine, 13: 1490-1495, 2007). Thus, if inhibiting Gls1 slows cyst growth in ADPKD, the present inventors will assess whether treatment with BPTES, BPTES analogs, or other gls1 inhibitors known to skilled practitioners and described herein affects the proliferation or apoptosis of renal cystic epithelia. Kidneys will be sectioned from both paraffin blocks and frozen sections (depending upon the antibody) and stained for a number of markers. Proliferation of cyst epithelia will be assessed by Ki-67 staining, and apoptosis by tunnel and by caspase 3 staining (Zhdanova et al. 2011, Kidney International 80:719-730).

mTor Activation: mTor activation will be assessed as described (Takiar et al. Proc Nati Acad Sci USA, 108: 2462-2467, 2011; the entire content of which is incorporated herein by reference). If glutamine metabolism is critical for mTor activation, the present inventors expect BAPTES treated animals to have decreased staining of cyst lining epithelia with anti pS6K, pS6, and p4EBP1 antibodies.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for treating autosomal dominant polycystic kidney disease, the method comprising administering to a subject in need thereof a therapeutically effective amount of an inhibitor of glutaminase 1 activity, wherein the inhibitor of glutaminase 1 activity is bis-2-(5-phenylacetamido-1,2,4-thiadiazol-2-yl)ethyl sulfide (BPTES) or an analog thereof, or a composition of BPTES or an analog thereof.

2. A method for inhibiting growth of kidney cysts in a subject afflicted with autosomal dominant polycystic kidney disease, the method comprising administering to a subject in need thereof a therapeutically effective amount of an inhibitor of glutaminase 1 activity, wherein the inhibitor of glutaminase 1 activity is bis-2-(5-phenylacetamido-1,2,4-thiadiazol-2-ypethyl sulfide (BPTES) or an analog thereof, or a composition of BPTES or an analog thereof.

3. A method for slowing progression of kidney disease in a subject afflicted with autosomal dominant polycystic kidney disease, the method comprising administering to a subject in need thereof a therapeutically effective amount of an inhibitor of glutaminase 1 activity, wherein the inhibitor of glutaminase 1 activity is bis-2-(5-phenylacetamido -1,2,4-thiadiazol-2-yl)ethyl sulfide (BPTES) or an analog thereof, or a composition of BPTES or an analog thereof.

4. The method of claim 1, wherein the subject is a mammal.

5. The method of claim 4, wherein the mammal is a human.

6. The method of claim 1, further comprising administering a therapeutically effective amount of at least one therapeutic agent selected from the group consisting of a vasopressin receptor antagonist, an HDAC inhibitor, a Src inhibitor, a Sirtuin 1 inhibitor, a tumor necrosis factor inhibitor, an epidermal growth factor inhibitor, an epidermal growth factor receptor inhibitor, a HER2 inhibitor, a Braf inhibitor, an inhibitor of hepatocyte growth factor, and an inhibitor of hepatocyte growth factor receptor cMET.

7. The method of claim 6, wherein the vasopressin receptor antagonist is tolvaptan or a mTor inhibitor.

8. The method of claim 1, wherein the inhibitor of glutaminase 1 activity or the composition thereof is administered orally.

9. The method of claim 1, wherein the subject is evaluated to determine if glutaminase 1 activity is elevated in the kidneys of the subject.

10. The method of claim 1, wherein the BPTES analog is a water soluble analog of BPTES.

11. The method of claim 1, wherein the BPTES analog is a compound having the structure.

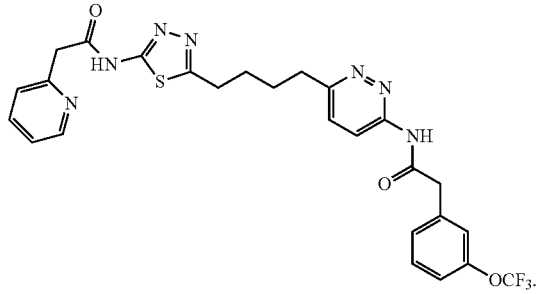 [SMILES: O=C(Cc1cccc(OC(F)(F)F)c1)Nc1ccc(CCCCc2nnc(NC(=O)Cc3ccccn3)s2)nn1]

* * * * *